US011155638B2

(12) United States Patent
Wands et al.

(10) Patent No.: US 11,155,638 B2
(45) Date of Patent: Oct. 26, 2021

(54) ANTI-CHI3L1 ANTIBODIES FOR THE DETECTION AND/OR TREATMENT OF NONALCOHOLIC FATTLY LIVER DISEASE/NONALCOHOLIC STEATONHEPATITIS AND SUBSEQUENT COMPLICATIONS

(71) Applicant: RHODE ISLAND HOSPITAL, Providence, RI (US)

(72) Inventors: Jack R. Wands, Pawtucket, RI (US); Rolf I. Carlson, Boston, MA (US)

(73) Assignee: RHODE ISLAND HOSPITAL, Providence, RI (US)

( * ) Notice: Subject to any disclaimer, the term of this patent is extended or adjusted under 35 U.S.C. 154(b) by 0 days.

(21) Appl. No.: 17/053,634

(22) PCT Filed: May 7, 2019

(86) PCT No.: PCT/US2019/031159
§ 371 (c)(1),
(2) Date: Nov. 6, 2020

(87) PCT Pub. No.: WO2019/217450
PCT Pub. Date: Nov. 14, 2019

(65) Prior Publication Data
US 2021/0230302 A1    Jul. 29, 2021

Related U.S. Application Data
(60) Provisional application No. 62/668,637, filed on May 8, 2018.

(51) Int. Cl.
*C07K 16/40*    (2006.01)
(52) U.S. Cl.
CPC ........ *C07K 16/40* (2013.01); *C07K 2317/565* (2013.01)
(58) Field of Classification Search
None
See application file for complete search history.

(56) References Cited

U.S. PATENT DOCUMENTS

| | | |
|---|---|---|
| 3,270,960 A | 9/1966 | Phillips |
| 3,773,919 A | 11/1973 | Boswell, II et al. |
| 4,172,896 A | 10/1979 | Uno et al. |
| 5,358,970 A | 10/1994 | Ruff et al. |
| 5,427,798 A | 6/1995 | Ludwig et al. |
| 5,541,231 A | 7/1996 | Ruff et al. |
| 5,639,641 A | 6/1997 | Pedersen et al. |
| 5,731,000 A | 3/1998 | Ruff et al. |
| 5,763,493 A | 6/1998 | Ruff et al. |
| 6,110,973 A | 8/2000 | Young |
| 6,180,370 B1 * | 1/2001 | Queen ............... C07K 16/2866 435/69.6 |
| 8,053,563 B2 * | 11/2011 | Bonnichsen ............ A61P 35/00 530/387.9 |
| 2002/0098190 A1 | 7/2002 | Chatterjee et al. |
| 2003/0211106 A1 | 11/2003 | Tornetta et al. |
| 2008/0038257 A1 | 2/2008 | Han et al. |
| 2011/0020349 A1 | 1/2011 | Gruber et al. |
| 2017/0107297 A1 | 4/2017 | Chang et al. |
| 2019/0119405 A1 | 4/2019 | Elias et al. |

FOREIGN PATENT DOCUMENTS

| | | |
|---|---|---|
| CN | 104004080 A | 8/2014 |
| EP | 0332424 A2 | 9/1989 |
| EP | 0239400 B1 | 8/1994 |
| EP | 0338745 B1 | 3/1995 |
| WO | 89/09622 A1 | 10/1989 |
| WO | 92/22653 A1 | 12/1992 |
| WO | 93/21319 A1 | 10/1993 |
| WO | 2018/014068 A1 | 1/2018 |
| WO | 2018/207638 A1 | 11/2018 |

OTHER PUBLICATIONS

Kipriyanov, Sergey M., and Fabrice Le Gall. "Generation and production of engineered antibodies." Molecular biotechnology 26.1 (2004): 39-60. (Year: 2004).*
Janeway, A. C., et al. "Immunobiology: the immune system in health and disease. London." Current Biology (1997): 3:1-3:11. (Year: 1997).*
Deutscher's, "[8] Maintaining protein stability", Methods in Enzymology, vol. 182, 1990, pp. 83-89.
International Search Report and Written Opinion received for PCT Patent International Application No. PCT/US2019/031159, dated Sep. 17, 2019, 12 pages.
Lewis, "Controlled Release of Pesticides and Pharmaceuticals", Plenum Press, New York, 1981.
Merck, "The Merck Manual of Diagnosis and Therapy" 19th Edition, Aug. 1, 2011.
Pearson et al. "Improved Tools for Biological Sequence Comparison", Proceedings of the National Academy of Sciences of the United States of America, vol. 85, Apr. 1988, pp. 2444-2448.
Porter et al. "The Encyclopedia of Molecular Biology", Blackwell Science Ltd., 1994.
Promrat et al. "Randomized Controlled Trial Testing the Effects of Weight Loss on Nonalcoholic Steatohepatitis (NASH)", Hepatology, vol. 51, Issue 1, Jan. 2010, pp. 121-129.

(Continued)

*Primary Examiner* — Michael Szperka
*Assistant Examiner* — Lia E Taylor
(74) *Attorney, Agent, or Firm* — Adler Pollock & Sheehan P.C.

(57) ABSTRACT

The present disclosure relates to antibodies that bind human chitinase-3-like protein 1 (CHI3L1) and uses thereof. In aspects, the antibodies are useful in compositions and methods for detecting and/or treating nonalcoholic steatohepatitis (NAFLD) or nonalcoholic fatty liver disease (NASH) in a subject, as well as subsequent complications of untreated progression in the liver of a subject, such as liver cirrhosis and/or a hepatocellular carcinoma.

7 Claims, 5 Drawing Sheets
Specification includes a Sequence Listing.

(56) References Cited

OTHER PUBLICATIONS

Scopes, "Protein Purification: Principles and Practice", 3rd Edition, Springer, NY, 1994.
Urquhart et al. "Rate-Controlled Delivery Systems in Drug and Hormone Research", Annual Review of Pharmacology and Toxicology, vol. 24, Apr. 1984, pp. 199-236.

* cited by examiner

ANTI-CHI3L1 ANTIBODIES FOR THE DETECTION AND/OR TREATMENT OF NONALCOHOLIC FATTLY LIVER DISEASE/NONALCOHOLIC STEATONHEPATITIS AND SUBSEQUENT COMPLICATIONS

CROSS REFERENCE TO RELATED APPLICATIONS

The instant application claims the benefit of priority to provisional application U.S. Ser. No. 62/668,637, filed May 8, 2018, the disclosures of which is incorporated by reference as if fully set forth herein in its entirety.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Apr. 30, 2018, is named "SEQENCE LISTING_ST25" and is 16 KB bytes in size.

FIELD OF THE INVENTION

The present disclosure generally relates to antibodies that bind human chitinase-3-like protein 1 (CHI3L1) and uses thereof. In aspects, the antibodies are useful in compositions and methods for detecting and/or treating nonalcoholic fatty liver disease (NAFLD) or nonalcoholic steatohepatitis (NASH) in a subject, as well as subsequent complications of untreated progression in the liver of a subject, such as liver cirrhosis and hepatocellular carcinoma (HCC).

BACKGROUND OF THE INVENTION

NAFLD combined with its severe and progressive form, called NASH, are the most common causes of chronic liver diseases in the world and generally are associated with obesity, type II diabetes, high blood pressure, high lipid content of the blood and unhealthy high-fat diets. The incidence of NAFLD is estimated to be as high as 25% of the population in the United States, as well as in some countries in Asia and Europe. The progressive form of NAFLD is represented by NASH, which occurs in approximately 20% of those individuals. NAFLD is generally thought to be benign and reversible under most circumstances, while NASH is characterized by progressive hepatic inflammation, steatosis, hepatocyte degeneration, fibrosis, progression to cirrhosis and even the development of HCC in a certain proportion of individuals. The seriousness of NASH is also reflected in children who are estimated to have an incidence of NAFLD as approximately 10-12% in the U.S.A., as some children will progress to end-stage liver diseases. The primary prognostic indicator in NAFLD/NASH is the presence of hepatic fibrosis, as many such individuals may eventually develop cirrhosis and even HCC, and thus become candidates for hepatic transplantation. Recent studies demonstrate that the degree of fibrosis, independent of any other pathologic features in the liver, may determine mortality rates in NAFLD/NASH. Because of the high prevalence of NAFLD/NASH in various countries of the world, it is anticipated that there will be a tremendous medical economic burden to patients and healthcare systems.

The gold standard for assessing the extent and severity of NAFLD/NASH requires evaluation of a liver biopsy, which is invasive, painful, expensive, and associated with bleeding complications and rarely death. Evaluation of a liver biopsy can determine the degree of steatosis (fat deposition), the severity of inflammation, the presence of hepatocyte degeneration (caused by chronic injury), as well as the presence or absence of fibrosis/cirrhosis. Accordingly, on-going need exists for alternative tests, such as simple and accurate blood tests, for biomarkers that are related to the progression of NAFLD/NASH, as well as subsequent complications of untreated progression in the liver of a subject, such as liver cirrhosis and HCC.

BRIEF SUMMARY OF THE INVENTION

Accordingly, the presently-disclosed subject matter relates to antibodies that bind to human CHI3L1 and uses thereof. In accordance with various embodiments of the present disclosure, the antibodies are useful in compositions and methods for detecting and/or treating NAFLD or NASH in a subject, as well as subsequent complications of untreated progression in the liver of a subject, such as liver cirrhosis and/or HCC.

In various embodiments, an antibody that binds to human CHI3L1 is provided, the antibody comprising a light chain and a heavy chain, wherein the light chain comprises a light chain variable region (LCVR) and the heavy chain comprises a heavy chain variable region (HCVR), wherein the LCVR comprises complementarity determining regions LCDR1, LCDR2, and LCDR3, and the HCVR comprises complementarity determining regions HCDR1, HCDR2, and HCDR3, wherein LCDR1 is SEQ ID NO:6, LCDR2 is SEQ ID NO:7, LCDR3 is SEQ ID NO:8, HCDR1 is SEQ ID NO:3, HCDR2 is SEQ ID NO:4, and HCDR3 is SEQ ID NO:5.

In some embodiments, an antibody that binds to human CHI3L1 is provided, the antibody comprising a light chain and a heavy chain, wherein the light chain comprises a LCVR and the heavy chain comprises a HCVR, wherein the LCVR comprises amino acid sequence SEQ ID NO: 10 and the HCVR comprises amino acid sequence SEQ ID NO: 9.

In some embodiments, an antibody that binds to human CHI3L1 is provided, the antibody comprising a light chain and a heavy chain, wherein the light chain comprises amino acid sequence SEQ ID NO: 12 and the heavy chain comprises amino acid sequence SEQ ID NO: 11.

In some embodiments, an antibody that binds to human CHI3L1 is provided, the antibody comprising two light chains and two heavy chains, wherein each light chain comprises amino acid sequence SEQ ID NO: 12 and each heavy chain comprises SEQ ID NO: 11.

In some embodiments, a DNA molecule is provided, the DNA molecule comprising a polynucleotide sequence encoding a light chain polypeptide having the amino acid sequence SEQ ID NO: 12.

In some embodiments, a DNA molecule is provided, the DNA molecule comprising a polynucleotide sequence encoding a heavy chain polypeptide having the amino acid sequence SEQ ID NO: 11.

In some embodiments, a recombinant host cell is provided, the recombinant host cell comprising the DNA molecules of the two previous embodiments, which cell is capable of expressing an antibody comprising a heavy chain and a light chain, wherein the amino acid sequence of the heavy chain is SEQ ID NO: 11 and the amino acid sequence of the light chain is SEQ ID NO: 12.

In some embodiments, a process for producing an antibody that binds to human CHI3L1 comprising a heavy chain and a light chain is provided, wherein the heavy chain comprises amino acid sequence SEQ ID NO: 11 and the light chain comprises the amino acid sequence of SEQ ID NO: 12, said process comprising the steps of: (a) cultivating a recombinant host cell of the previous embodiment, under conditions such that said antibody is expressed; and (b) recovering from said host cell the expressed antibody. In some embodiments, an antibody produced by the process is provided.

In various embodiments, an antibody that binds to human CHI3L1 is provided, the antibody comprising a light chain and a heavy chain, wherein the light chain comprises a light chain variable region (LCVR) and the heavy chain comprises a heavy chain variable region (HCVR), wherein the LCVR comprises complementarity determining regions LCDR1, LCDR2, and LCDR3, and the HCVR comprises complementarity determining regions HCDR1, HCDR2, and HCDR3, wherein LCDR1 is SEQ ID NO:16, LCDR2 is SEQ ID NO:17, LCDR3 is SEQ ID NO:18, HCDR1 is SEQ ID NO:13, HCDR2 is SEQ ID NO:14, and HCDR3 is SEQ ID NO:15.

In some embodiments, an antibody that binds to human CHI3L1 is provided, the antibody comprising a light chain and a heavy chain, wherein the light chain comprises a LCVR and the heavy chain comprises a HCVR, wherein the LCVR comprises amino acid sequence SEQ ID NO: 20 and the HCVR comprises amino acid sequence SEQ ID NO: 19

In some embodiments, an antibody that binds to human CHI3L1 is provided, the antibody comprising a light chain and a heavy chain, wherein the light chain comprises amino acid sequence SEQ ID NO: 22 and the heavy chain comprises amino acid sequence SEQ ID NO: 21.

In some embodiments, an antibody that binds to human CHI3L1 is provided, the antibody comprising two light chains and two heavy chains, wherein each light chain comprises amino acid sequence SEQ ID NO: 22 and each heavy chain comprises SEQ ID NO: 21.

In some embodiments, a DNA molecule is provided, the DNA molecule comprising a polynucleotide sequence encoding a light chain polypeptide having the amino acid sequence SEQ ID NO: 22.

In some embodiments, a DNA molecule is provided, the DNA molecule comprising a polynucleotide sequence encoding a heavy chain polypeptide having the amino acid sequence SEQ ID NO: 21.

In some embodiments, a recombinant host cell is provided, the recombinant host cell comprising the DNA molecules of the two previous embodiments, which cell is capable of expressing an antibody comprising a heavy chain and a light chain, wherein the amino acid sequence of the heavy chain is SEQ ID NO: 21 and the amino acid sequence of the light chain is SEQ ID NO: 22.

In some embodiments, a process for producing an antibody that binds to human CHI3L1 comprising a heavy chain and a light chain is provided, wherein the heavy chain comprises amino acid sequence SEQ ID NO: 21 and the light chain comprises the amino acid sequence of SEQ ID NO: 22, said process comprising the steps of: (a) cultivating a recombinant host cell of the previous embodiment, under conditions such that said antibody is expressed; and (b) recovering from said host cell the expressed antibody. In some embodiments, an antibody produced by the process is provided.

In some embodiments, a pharmaceutical composition comprising at least one antibody of the instant disclosure and one or more pharmaceutically acceptable carriers, diluents, or excipients is provided.

In various embodiments an assay is provided, the assay comprising: (i) measuring, in a sample obtained from a subject, a level of CHI3L1, wherein said measuring comprises incubating the sample with an antibody in an article with an immobilized antibody of any one of claims 1-4; (ii) comparing the level of CHI3L1 with a reference level; and (iii) identifying the subject as (a) having NAFLD or NASH if the level of CHI3L1 is above the reference level; or (b) not having NAFLD or NASH if the level of CHI3L1 is at or below the reference level. In some aspects, the reference level is about 2.0 ng/30 µL serum. In some aspects, when the level of CHI3L1 is above the reference level, the assay further comprises providing a treatment appropriate for treating NAFLD or NASH. In some aspects, the treatment comprises administering a CHI3L1 inhibitor. In some aspects, the CHI3L1 inhibitor comprises at least one antibody that binds to human CHI3L1 of the instant disclosure.

In various embodiments, as assay is provided, the assay comprising: (i) measuring, in a sample obtained from a subject, a level of CHI3L1, wherein said measuring comprises incubating the sample with an antibody in an article with an immobilized antibody of any one of claims 1-4; (ii) comparing the level of CHI3L1 with a reference level; and (iii) identifying the subject as (a) having liver cirrhosis if the level of CHI3L1 is above the reference level; or (b) not having liver cirrhosis if the level of CHI3L1 is at or below the reference level. In some aspects, the reference level is about 2.0 ng/30 µL serum. In some aspects, when the level of CHI3L1 is above the reference level, the assay further comprises providing a treatment appropriate for treating liver cirrhosis. In some aspects, the treatment comprises administering a CHI3L1 inhibitor. In some aspects, the CHI3L1 inhibitor comprises at least one antibody that binds to human CHI3L1 of the instant disclosure.

In some embodiments, an assay is provided, the assay comprising: (i) measuring, in a sample obtained from a subject, a level of CHI3L1, wherein said measuring comprises incubating the sample with an antibody in an article with an immobilized antibody of any one of claims 1-4; (ii) comparing the level of CHI3L1 with a reference level; and (iii) identifying the subject as (a) having HCC if the level of CHI3L1 is above the reference level; or (b) not having HCC if the level of CHI3L1 is at or below the reference level. In some aspects, the reference level is about 2.0 ng/30 µL serum. In some aspects, when the level of CHI3L1 is above the reference level, the assay further comprises providing a treatment appropriate for treating HCC. In some aspects, the treatment comprises administering a CHI3L1 inhibitor. In some aspects, the CHI3L1 inhibitor comprises at least one antibody that binds to human CHI3L1 of the instant disclosure.

In some embodiments, a method of monitoring treatment efficacy in a subject having NAFLD or NASH is provided, the method comprising: (i) measuring, at a first time point, a first level of CHI3L1 in a first sample obtained from the subject, wherein said measuring comprises incubating the sample with an antibody in an article with an immobilized antibody of any one of claims 1-4; (ii) administering to the subject a therapeutic agent for treating NAFLD or NASH; and (iii) measuring, at a second time point, a second level of CHI3L1 in a second sample obtained from the subject, wherein said measuring comprises incubating the sample with an antibody in an article with an immobilized antibody of any one of claims 1-4, wherein the second time point is later than the first time point and after said administering, and wherein if the second level is significantly lower than the first level, then the treatment is considered to be effective. In some aspects, the therapeutic agent is a CHI3L1 inhibitor. In some aspects, the CHI3L1 inhibitor comprises at least one antibody that binds to human CHI3L1 of the instant disclosure.

In some embodiments, a method of treating NAFLD or NASH in a subject is provided, the method comprising administering a therapeutically-effective amount of at least one antibody that binds to human CHI3L1 of the instant disclosure to the subject.

In some aspects, a method of treating liver cirrhosis in a subject is provided, the method comprising administering a therapeutically-effective amount of at least one antibody that binds to human CHI3L1 of the instant disclosure to the subject.

In some aspects, a method of treating HCC in a subject is provided, the method comprising administering a therapeutically-effective amount of at least one antibody that binds to human CHI3L1 of the instant disclosure to the subject.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals and in which.

DETAILED DESCRIPTION OF THE INVENTION

Figure 1:
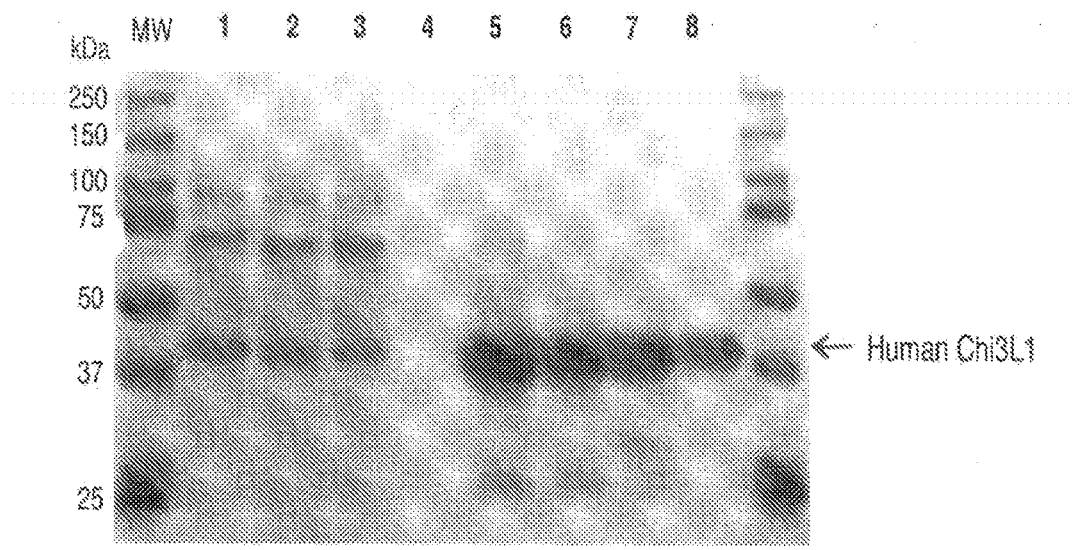
FIG. 1 depicts the expression and purification of human CHI3L1 protein. The immunogenicity of the recombinant CHI3L1 protein is demonstrated by a commercial antibody against CHI3L1 protein.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein. While the processes and compositions are described as using a specific order of individual steps or specific materials, it is appreciated that steps or materials may be interchangeable such that the description of the invention may include multiple steps or parts arranged in many ways as is readily appreciated by one of skill in the art.

Definitions

As used herein, singular forms "a," "an" and "the" include plural referents unless the context clearly dictates otherwise. Thus, for example, reference to "a structured bottom surface" includes examples having two or more such "structured bottom surfaces" unless the context clearly indicates otherwise.

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, "have", "has", "having", "include", "includes", "including", "comprise", "comprises", "comprising" or the like are used in their open ended inclusive sense, and generally mean "include, but not limited to", "includes, but not limited to", or "including, but not limited to".

"Optional" or "optionally" means that the subsequently described event, circumstance, or component, can or cannot occur, and that the description includes instances where the event, circumstance, or component, occurs and instances where it does not.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the inventive technology.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

Also, herein, the recitations of numerical ranges by endpoints include all numbers subsumed within that range (e.g., 1 to 5 includes 1, 1.5, 2, 2.75, 3, 3.80, 4, 5, etc.). It should be further understood that every numerical range given throughout this specification will include every narrower numerical range that falls within such broader numerical range, as if such narrower numerical ranges were all expressly written herein. Where a range of values is "greater than", "less than", etc. a particular value, that value is included within the range.

As used herein, the terms "disease", "disorder", or "condition" are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, or affectation.

As used herein, "nonalcoholic fatty liver disease" or "NAFLD" refers to a benign and nonprogressive disease or disorder characterized in abnormal fat deposition (i.e., steatosis) in the liver not due to excessive alcohol use.

As used herein, "nonalcoholic steatohepatitis" or "NASH" refers to a progressive disease or disorder characterized by inflammation of the liver in combination with fatty liver. It resembles alcoholic liver disease, but occurs in people who drink little or no alcohol. NASH can lead to fibrosis, cirrhosis, end stage liver disease, hepatic failure, and hepatocellular carcinoma.

As used herein, the term "long-term" administration means that the therapeutic agent or drug is administered for a period of at least 12 weeks. This includes that the therapeutic agent or drug is administered such that it is effective over, or for, a period of at least 12 weeks and does not necessarily imply that the administration itself takes place for 12 weeks, e.g., if sustained release compositions or long acting therapeutic agent or drug is used. Thus, the subject is treated for a period of at least 12 weeks. In many cases, long-term administration is for at least 4, 5, 6, 7, 8, 9 months or more, or for at least 1, 2, 3, 5, 7 or 10 years, or more.

As used herein, "CHI3L1," "chitinase-3-like protein 1," or "YKL-40" refers to a ~40 kDa glycoprotein secreted by at least macrophages, chondrocytes, neutrophils, synovial cells, and some cancer cells. CHI3L1 does not have chitinase activity, is a Th2 promoting cytokine, has been linked to the AKT anti-apoptotic signaling pathway and induces the migration of astrocytes. The sequences of CHI3L1 expression products are known for a number of species, e.g., human CHI3L1 (NCBI Gene ID NO: 1116) mRNA (SEQ ID NO: 2; NCBI Ref Seq: NM 001276) and polypeptide (SEQ ID NO: 1; NCBI Ref Seq: NP 001267). The activity of CHI3L1 can be measured, e.g., by measuring the anti-apoptotic effects of CHI3L1, or by assaying promotion of Th2 cytokine production.

As used herein, the term "inhibitor" refers to an agent which can decrease the expression and/or activity of the targeted expression product (e.g., mRNA encoding the target or a target polypeptide), e.g., by at least 10% or more, e.g., by 10% or more, 50% or more, 70% or more, 80% or more, 90% or more, 95% or more, or 98% or more. The efficacy of an inhibitor of, for example, CHI3L1, e.g., its ability to decrease the level and/or activity of CHI3L1 can be determined, e.g., by measuring the level of an expression product of CHI3L1 and/or the activity of CHI3L1. Methods for measuring the level of a given mRNA and/or polypeptide are known to one of skill in the art, e.g., RT-PCR can be used to determine the level of RNA, and Western blotting or immunoassay with an antibody (e.g., an anti-CHI3L1 antibody) can be used to determine the level of a polypeptide. The activity of, e.g., CHI3L1 can be determined using methods known in the art. In some embodiments, the inhibitor can be an inhibitory nucleic acid; an aptamer; an antibody reagent; an antibody; or a small molecule.

As used herein, the term "article", "cell culture article", or the like, means any container useful for in vitro experiments with cells, including culturing cells, and includes plates, wells, flasks, multi-well plates, multi-layer flasks, and perfusion systems which provide an environment for cell culture.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein. Preferably, the subject is a mammal. The mammal can be a human, non-human primate, mouse, rat, dog, cat, horse, or cow, but is not limited to these examples. Mammals other than humans can be advantageously used as subjects that represent animal models of NASH. A subject can be male or female.

A subject can be one who has been previously diagnosed with or identified as suffering from or having a condition in need of treatment (e.g., NAFLD and/or NASH) or one or more complications related to such a condition, and optionally, have already undergone treatment for NAFLD and/or NASH or the one or more complications related to NAFLD and/or NASH (e.g., liver cirrhosis and/or hepatocellular carcinoma). Alternatively, a subject can also be one who has not been previously diagnosed as having, e.g., NAFLD and/or NASH or one or more complications related to NAFLD and/or NASH. For example, a subject can be one who exhibits one or more risk factors for NAFLD and/or NASH or one or more complications related to NAFLD and/or NASH or a subject who does not exhibit risk factors.

A "subject in need" of treatment for a particular condition can be a subject having that condition, diagnosed as having that condition, or at elevated risk of developing that condition.

The term "sample", "biological sample", or "test sample" as used herein denotes a sample taken or isolated from a biological organism, e.g., a blood or plasma sample from a subject. Exemplary biological samples include, but are not limited to, a biofluid sample; serum; plasma; urine; saliva; and/or tissue sample etc. The term also includes a mixture of the above-mentioned samples. The term "test sample" also includes untreated or pretreated (or pre-processed) biological samples. In some embodiments, a test sample can comprise cells from a subject. In some embodiments, the test sample can be a blood sample. In some embodiments, the test sample can be a plasma sample. In some embodiments, the test sample can be a serum sample.

The test sample can be obtained by removing a sample from a subject, but can also be accomplished by using previously sample (e.g., isolated at a prior time point and isolated by the same or another person). In addition, the test sample can be freshly collected or a previously collected sample.

As used herein, the term "isolated" refers to a protein, peptide, or nucleic acid which is free or substantially free from any other macromolecular species found in a cellular environment. "Substantially free" as used herein means the protein, peptide, or nucleic acid of interest comprises more than 80% (on a molar bases) of the macromolecular species present, more than 90%, more than 95%, or more than 99%.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, "expression level" refers to the number of mRNA molecules and/or polypeptide molecules encoded by a given gene that are present in a cell or sample. Expression levels can be increased or decreased relative to a reference level.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g., NAFLD, NASH, and subsequent complications of untreated progression in the liver of a subject, such as liver cirrhosis and/or HCC. The term "treating" includes reducing or alleviating at least one adverse effect or symptom of a condition, disease or disorder, e.g., NAFLD, NASH, and subsequent complications of untreated progression in the liver of a subject, such as liver cirrhosis and/or HCC. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g., a carrier commonly used in the pharmaceutical industry.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "effective amount" as used herein refers to the amount of a therapy needed to alleviate at least one or more symptoms of the disease or disorder (e.g., NAFLD, NASH, and subsequent complications of untreated progression in the liver of a subject, such as liver cirrhosis and/or HCC), and relates to a sufficient amount of pharmaceutical composition to provide the desired effect. The term "therapeutically-effective amount" therefore refers to an amount of a therapy that is sufficient to cause a particular effect when administered to a typical subject. An effective amount as used herein, in various contexts, would also include an amount sufficient to delay the development of a symptom of the disease, alter the course of a symptom of the disease (for example but not limited to, slowing the progression of a symptom of the disease), or reverse a symptom of the disease. It will be appreciated that there will be many ways known in the art to determine the effective amount for a given application. For example, the pharmacological methods for dosage determination may be used in the therapeutic context. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intrahepatic, intraperitoneal, transtracheal, subcutaneous, subcuticular, intraarticular, sub capsular, subarachnoid, intraspinal, intracerebrospinal, and intrasternal injection and infusion. The administration can be systemic or local.

The term "statistically significant" or "significantly" refers to statistical significance which in certain aspects may mean a two standard deviation (2SD) or greater difference.

As used herein, the term "significantly" should be interpreted as if modified by the term "statistically".

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

While various features, elements or steps of particular embodiments may be disclosed using the transitional phrase "comprising," it is to be understood that alternative embodiments, including those that may be described using the transitional phrases "consisting" or "consisting essentially of," are implied.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-micro emulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragées, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropyl methyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragées, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropyl methyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, micro-emulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intraocular (such as intravitreal), intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically-acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art. See, e.g., Isselbacher et al. (1996) Harrison's Principles of Internal Medicine 13 ed., 1814-1882.

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In other embodiments, the active compound will be administered once daily.

The patient receiving this treatment is any animal in need, including primates, in particular humans; and other mammals such as equines bovine, porcine, sheep, feline, and canine; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, l-ascorbic acid, l-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

CHI3L1 Antibodies

The presently-disclosed data demonstrates that the antibodies that bind to human CHI3L1 of the present invention are useful in compositions and methods for detecting NAFLD or NASH in a subject, as well as subsequent complications of untreated progression in the liver of a subject, such as liver cirrhosis and/or HCC. Unlike some prior art antibodies that bind to human CHI3L1, the instantly-disclosed antibodies can be used to clearly distinguish between healthy subjects and diseased subjects, such as those suffering from NAFLD/NASH as well as liver cirrhosis and/or HCC. Prior to the instant-disclosure, there has been no reliable method to accurately determine the presence of this protein in blood of individuals with NAFLD/NASH. The only FDA approved treatment currently for NAFLD/NASH is lifestyle modification, including weight loss and exercise. Bariatric surgery is another drastic weight loss approach that may also be utilized for treatment of this disease, but it is invasive and has serious complications. It is highly likely that newer, pharmacologic therapies will be developed in the future. As such, the present invention will be valuable for identifying individuals with NAFLD/NASH and monitoring their response to therapy. It may help predict long-term outcome and serve as a promising end point to measure therapeutic effects of new agents.

Accordingly, the present invention provides an antibody (herein "AB1" or "CH568") that binds to human CHI3L1, the antibody comprising a light chain and a heavy chain, wherein the light chain comprises a LCVR and the heavy chain comprises a HCVR, wherein the LCVR comprises complementarity determining regions LCDR1, LCDR2, and LCDR3, and the HCVR comprises complementarity determining regions HCDR1, HCDR2, and HCDR3, wherein LCDR1 is SEQ ID NO:6, LCDR2 is SEQ ID NO:7, LCDR3 is SEQ ID NO:8, HCDR1 is SEQ ID NO:3, HCDR2 is SEQ ID NO:4, and HCDR3 is SEQ ID NO:5.

In some aspects of the previous embodiment, the antibody comprises a light chain and a heavy chain, wherein the light chain comprises a LCVR and the heavy chain comprises a HCVR, wherein the LCVR comprises amino acid sequence SEQ ID NO: 10 and the HCVR comprises amino acid sequence SEQ ID NO: 9

In further aspects of the previous embodiments, the antibody comprises a light chain and a heavy chain, wherein the light chain comprises amino acid sequence SEQ ID NO: 12 and the heavy chain comprises amino acid sequence SEQ ID NO: 11.

In even further aspects of the previous embodiments, the antibody comprises two light chains and two heavy chains, wherein each light chain comprises amino acid sequence SEQ ID NO: 12 and each heavy chain comprises SEQ ID NO: 11.

In aspects of the previous embodiments, the antibody is an IgG type antibody. In further aspects, the antibody comprises a kappa light chain. In even further aspects, the antibody is a murine antibody.

Table 1 shows the amino acid sequences of AB1 (CH568).

TABLE 1

| SEQ ID NO: | Identity | Sequence |
|---|---|---|
| 3 | Heavy Chain - CDR1 | SYNMH |
| 4 | Heavy Chain - CDR2 | LISPGNGDTSYNQKFKG |
| 5 | Heavy Chain - CDR3 | GGPTVVAHYYAMDY |
| 6 | Light Chain - CDR1 | SASSRVSYMH |
| 7 | Light Chain - CDR2 | DTSN LAS |
| 8 | Light Chain - CDR3 | QQWSSNPLT |
| 9 | Heavy Chain Variable Domain | QVQLQQTGAELVKPGASVKMSCKASGYTFTSYNMHWLKQTPGQGLEWIGLISPGNGDTSYNQKFKGKATLTADKSSNTAYMQLSSLTSEDSAVYFCARGGPTVVAHYYAMDYWGQGTSVTVSS |

TABLE 1-continued

| SEQ ID NO: | Identity | Sequence |
|---|---|---|
| 10 | Light Chain Variable Domain | QIVLTQSPAIMSASPGERVTMTCSASSRVSYMHWYQQKSGT SPKRWIYDTSNLASGVPARFSGSGSGTSYSLTISTMEAEDAA TYYCQQWSSNPLTFGAGTKLELK |
| 11 | Heavy Chain | QVQLQQTGAELVKPGASVKMSCKASGYTFTSYNMHWLKQT PGQGLEWIGLISPGNGDTSYNQKFKGKATLTADKSSNTAYM QLSSLTSEDSAVYFCARGGPTVVAHYYAMDYWGQGTSVTV SSAKTTPPSVYPLAPGSAAQTNSMVTLGCLVKGYFPEPVTVT WNSGSLSSGVHTFPAVLQSDLYTLSSSVTVPSSTWPSETVT CNVAHPASSTKVDKKIVPRDCGCKPCICTVPEVSSVFIFPPKP KDVLTITLTPKVTCVVVDISKDDPEVQFSWFVDDVEVHTAQT QPREEQFNSTFRSVSELPIMHQDWLNGKEFKCRVNSAAFPA PIEKTISKTKGRPKAPQVYTIPPPKEQMAKDKVSLTCMITDFF PEDITVEWQWNGQPAENYKNTQPIMDTDGSYFVYSKLNVQK SNWEAGNTFTCSVLHEGLHNHHTEKSLSHSPGK |
| 12 | Light Chain | QIVLTQSPAIMSASPGERVTMTCSASSRVSYMHWYQQKSGT SPKRWIYDTSNLASGVPARFSGSGSGTSYSLTISTMEAEDAA TYYCQQWSSNPLTFGAGTKLELKRADAAPTVSIFPPSSEQLT SGGASVVCFLNNFYPKDINVKWKIDGSERQNGVLNSWTDQD SKDSTYSMSSTLTLTKDEYERHNSYTCEATHKTSTSPIVKSF NRNEC |

The present invention further provides an antibody (herein "AB2" or "CHXI3B6-6") that binds to human CHI3L1, the antibody comprising a light chain and a heavy chain, wherein the light chain comprises a LCVR and the heavy chain comprises a HCVR, wherein the LCVR comprises complementarity determining regions LCDR1, LCDR2, and LCDR3, and the HCVR comprises complementarity determining regions HCDR1, HCDR2, and HCDR3, wherein LCDR1 is SEQ ID NO:16, LCDR2 is SEQ ID NO:17, LCDR3 is SEQ ID NO:18, HCDR1 is SEQ ID NO:13, HCDR2 is SEQ ID NO:14, and HCDR3 is SEQ ID NO:15.

In some aspects of the previous embodiment, the antibody comprises a light chain and a heavy chain, wherein the light chain comprises a LCVR and the heavy chain comprises a HCVR, wherein the LCVR comprises amino acid sequence SEQ ID NO: 20 and the HCVR comprises amino acid sequence SEQ ID NO: 19.

In further aspects of the previous embodiments, the antibody comprises a light chain and a heavy chain, wherein the light chain comprises amino acid sequence SEQ ID NO: 22 and the heavy chain comprises amino acid sequence SEQ ID NO: 21.

In even further aspects of the previous embodiments, the antibody comprises two light chains and two heavy chains, wherein each light chain comprises amino acid sequence SEQ ID NO: 22 and each heavy chain comprises SEQ ID NO: 21.

In aspects of the previous embodiments, the antibody is an IgG type antibody. In further aspects, the antibody comprises a kappa light chain. In even further aspects, the antibody is a murine antibody.

Table 2 shows the amino acid sequences of AB2 (CHXI3B6-6).

TABLE 2

| SEQ ID NO: | Identity | Sequence |
|---|---|---|
| 13 | Heavy Chain - CDR1 | DYSMH |
| 14 | Heavy Chain - CDR2 | WINTETGEPTYADDFKG |
| 15 | Heavy Chain - CDR3 | EYGNYEGFVY |
| 16 | Light Chain - CDR1 | RASKSVSTSGYSYMH |
| 17 | Light Chain - CDR2 | LASNLES |
| 18 | Light Chain - CDR3 | QHSRELPWT |
| 19 | Heavy Chain Variable Domain | QIQLVQSGPELKKPGETVKISCKASGYTFTDYSMHVVVKQTP GKGLKWMVWINTETGEPTYADDFKGRFAFSLETSASTAYLQI NNLKNEDTATYFCAREYGNYEGFVYWGQGTLVTVSA |
| 20 | Light Chain Variable Domain | DIVLTQSPASLAVSLGQRATISCRASKSVSTSGYSYMHWYQQ KPGQPPKLLIYLASNLESGVPARFSGSGSGTDFTLNIHPVEEE DAATYYCQHSRELPWTFGGGTKLEIK |
| 21 | Heavy Chain | QIQLVQSGPELKKPGETVKISCKASGYTFTDYSMHVVVKQTP GKGLKWMVWINTETGEPTYADDFKGRFAFSLETSASTAYLQI NNLKNEDTATYFCAREYGNYEGFVYWGQGTLVTVSAAKTTP PSVYPLAPGSAAQINSMVTLGCLVKGYFPEPVTVTWNSGSL SSGVHTFPAVLQSDLYTLSSSVTVPSSTWPSETVICNVAHPA SSTKVDKKIVPRDCGCKPCICTVPEVSSVFIFPPKPKDVLTITL TPKVTCVVVDISKDDPEVQFSWFVDDVEVHTAQTQPREEQF NSTFRSVSELPIMHQDWLNGKEFKCRVNSAAFPAPIEKTISKT KGRPKAPQVYTIPPPKEQMAKDKVSLTCMITDFFPEDITVEW QWNGQPAENYKNTQPIMDTDGSYFVYSKLNVQKSNWEAGN TFTCSVLHEGLHNHHTEKSLSHSPGK |

TABLE 2-continued

| SEQ ID NO: | Identity | Sequence |
| --- | --- | --- |
| 22 | Light Chain | DIVLTQSPASLAVSLGQRATISCRASKSVSTSGYSYMHWYQQ KPGQPPKLLIYLASNLESGVPARFSGSGSGTDFTLNIHPVEEE DAATYYCQHSRELPWTFGGGTKLEIKRADAAPTVSIFPPSSE QLTSGGASVVCFLNNFYPKDINVKWKIDGSERQNGVLNSWT DQDSKDSTYSMSSTLTLTKDEYERHNSYTCEATHKTSTSPIV KSFNRNEC |

The present invention also relates to polynucleotides encoding the above-described antibodies (e.g., AB1 and AB2) of the present invention.

In some embodiments, the present invention provides a DNA molecule comprising a polynucleotide sequence encoding a light chain polypeptide having the amino acid sequence SEQ ID NO: 12. In some embodiments, a DNA molecule is provided, the DNA molecule comprising a polynucleotide sequence encoding a heavy chain polypeptide having the amino acid sequence SEQ ID NO: 11.

In some embodiments, the present invention provides a polynucleotide sequence encoding an antibody of the present invention, wherein the LCVR is encoded by SEQ ID NO: 24 and the HCVR is encoded by SEQ ID NO: 23.

In further embodiments, the present invention provides a polynucleotide encoding an antibody of the present invention, wherein the light chain is encoded by SEQ ID NO: 26 and the heavy chain is encoded by SEQ ID NO: 25.

Table 3 shows the DNA sequences for expression of AB1 (CH568).

TABLE 3

| SEQ ID NO: | Identity | Sequence |
| --- | --- | --- |
| 23 | Heavy Chain Variable Domain | CAGGTGCAACTGCAGCAGACTGGGGCTGAGCTGGTGAAG CCTGGGGCCTCAGTGAAGATGTCCTGCAAGGCTTCTGGCT ACACATTTACCAGTTACAATATGCACTGGCTAAAGCAGACA CCTGGACAGGGCCTGGAATGGATTGGACTTATTTCTCCAG GAAATGGTGATACTTCCTACAATCAGAAGTTCAAAGGCAAG GCCACATTGACTGCAGACAAATCCTCCAACACAGCCTACAT GCAGCTCAGTAGCCTGACATCTGAGGACTCTGCGGTCTATT TCTGTGCAAGAGGGGGGCCTACGGTAGTAGCCCATTACTA TGCTATGGACTACTGGGGTCAGGGAACCTCAGTCACCGTC TCCTCA |
| 24 | Light Chain Variable Domain | CAAATTGTTCTCACCCAGTCTCCAGCAATCATGTCTGCATC CTCAGGGGAGAGGGTCACCATGACCTGCAGTGCCAGCTCA CGTGTAAGTTACATGCACTGGTACCAGCAGAAGTCAGGCA CCTCCCCCAAAAGATGGATTTATGACACATCCAACCTGGCT TCTGGAGTCCCTGCTCGCTTCAGTGGCAGTGGGTCTGGGA CCTCTTACTCTCTCACAATCAGCACCATGGAGGCTGAAGAT GCTGCCACTTATTACTGCCAGCAGTGGAGTAGTAACCCGCT CACGTTCGGTGCTGGGACCAAGCTGGAGCTGAAA |
| 25 | Heavy Chain | CAGGTGCMCTGCAGCAGACTGGGGCTGAGCTGGTGAAG CCTGGGGCCTCAGTGAAGATGTCCTGCAAGGCTTCTGGCT ACACATTTACCAGTTACAATATGCACTGGCTAAAGCAGACA CCTGGACAGGGCCTGGAATGGATTGGACTTATTTCTCCAG GAAATGGTGATACTTCCTACAATCAGAAGTTCAAAGGCAAG GCCACATTGACTGCAGACAAATCCTCCAACACAGCCTACAT GCAGCTCAGTAGCCTGACATCTGAGGACTCTGCGGTCTATT TCTGTGCAAGAGGGGGGCCTACGGTAGTAGCCCATTACTA TGCTATGGACTACTGGGGTCAGGGAACCTCAGTCACCGTC TCCTCAGCCAAAACGACACCCCCATCTGTCTATCCACTGGC CCCTGGATCTGCTGCCCAAACTAACTCCATGGTGACCCTG GGATGCCTGGTCAAGGGCTATTTCCCTGAGCCAGTGACAG TGACCTGGAACTCTGGATCCCTGTCCAGCGGTGTGCACAC CTTCCCAGCTGTCCTGCAGTCTGACCTCTACACTCTGAGCA GCTCAGTGACTGTCCCCTCCAGCACCTGGCCCAGCGAGAC CGTCACCTGCAACGTTGCCCACCCGGCCAGCAGCACCAAG GTGGACAAGAAAATTGTGCCCAGGGATTGTGGTTGTAAGC CTTGCATATGTACAGTCCCAGAAGTATCATCTGTCTTCATCT TCCCCCCAAAGCCCAAGGATGTGCTCACCATTACTCTGACT CCTAAGGTCACGTGTGTTGTGGTAGACATCAGCAAGGATG ATCCCGAGGTCCAGTTCAGCTGGTTTGTAGATGATGTGGA GGTGCACACAGCTCAGACGCAACCCCGGGAGGAGCAGTT CAACAGCACTTTCCGCTCAGTCAGTGAACTTCCCATCATGC ACCAGGACTGGCTCAATGGCAAGGAGTTCAAATGCAGGGT CAACAGTGCAGCTTTCCCTGCCCCCATCGAGAAAACCATCT CCAAAACCAAAGGCAGACCGAAGGCTCCACAGGTGTACAC CATTCCACCTCCCAAGGAGCAGATGGCCAAGGATAAAGTC AGTCTGACCTGCATGATAACAGACTTCTTCCCTGAAGACAT TACTGTGGAGTGGCAGTGGAATGGGCAGCCAGCGGAGAA CTACAAGAACACTCAGCCCATCATGGACACAGATGGCTCTT ACTTCGTCTACAGCAAGCTCAATGTGCAGAAGAGCAACTGG |

TABLE 3-continued

| SEQ ID NO: | Identity | Sequence |
|---|---|---|
| 26 | Light Chain | GAGGCAGGAAATACTTTCACCTGCTCTGTGTTACATGAGGG
CCTGCACAACCACCATACTGAGAAGAGCCTCTCCCACTCTC
CTGGTAAA
CAAATTGTTCTCACCCAGTCTCCAGCAATCATGTCTGCATC
TCCAGGGGAGAGGGTCACCATGACCTGCAGTGCCAGCTCA
CGTGTAAGTTACATGCACTGGTACCAGCAGAAGTCAGGCA
CCTCCCCCAAAAGATGGATTTATGACACATCCAACCTGGCT
TCTGGAGTCCCTGCTCGCTTCAGTGGCAGTGGGTCTGGGA
CCTCTTACTCTCACAATCAGCACCATGGAGGCTGAAGAT
GCTGCCACTTATTACTGCCAGCAGTGGAGTAGTAACCCGCT
CACGTTCGGTGCTGGGACCAAGCTGGAGCTGAAACGGGCT
GATGCTGCACCAACTGTATCCATCTTCCCACCATCCAGTGA
GCAGTTAACATCTGGAGGTGCCTCAGTCGTGTGCTTCTTGA
ACAACTTCTACCCCAAAGACATCAATGTCAAGTGGAAGATT
GATGGCAGTGAACGACAAAATGGCGTCCTGAACAGTTGGA
CTGATCAGGACAGCAAAGACAGCACCTACAGCATGAGCAG
CACCCTCACGTTGACCAAGGACGAGTATGAACGACATAACA
GCTATACCTGTGAGGCCACTCACAAGACATCAACTTCACCC
ATTGTCAAGAGCTTCAACAGGAATGAGTGT |

In some embodiments, the present invention provides a DNA molecule comprising a polynucleotide sequence encoding a light chain polypeptide having the amino acid sequence SEQ ID NO: 22. In some embodiments, a DNA molecule is provided, the DNA molecule comprising a polynucleotide sequence encoding a heavy chain polypeptide having the amino acid sequence SEQ ID NO: 21.

In some embodiments, the present invention provides a polynucleotide sequence encoding an antibody of the present invention, wherein the LCVR is encoded by SEQ ID NO: 28 and the HCVR is encoded by SEQ ID NO: 27.

In further embodiments, the present invention provides a polynucleotide encoding an antibody of the present invention, wherein the light chain is encoded by SEQ ID NO: 30 and the heavy chain is encoded by SEQ ID NO: 29.

Table 4 shows the DNA sequences for expression of AB2 (CHXI3B6-6).

TABLE 4

| SEQ ID NO: | Identity | Sequence |
|---|---|---|
| 27 | Heavy Chain Variable Domain | CAGATCCAGTTGGTGCAGTCTGGACCTGAGCTGAAGAAG
CCTGGAGAGACAGTCAAGATCTCCTGCAAGGCTTCTGGTT
ATACCTTCACAGACTATTCAATGCACTGGGTGAAACAGACT
CCAGGAAAGGGTTTAAAGTGGATGGTCTGGATAAACACTG
AGACTGGTGAGCCAACATATGCAGATGACTTCAAGGGACG
GTTTGCCTTCTCTTTGGAAACCTCTGCCAGCACCGCCTATT
TGCAGATCAACAACCTCAAAAATGAGGACACGGCTACATA
TTTCTGTGCTAGAGAGTATGGAAACTACGAGGGGTTTGTT
TACTGGGGCCAAGGGACTCTGGTCACTGTCTCTGCA |
| 28 | Light Chain Variable Domain | GACATTGTGCTGACACAGTCTCCTGCTTCCTTAGCTGTATC
TCTGGGGCAGAGGGCCACCATCTCATGCAGGGCCAGCAA
AAGTGTCAGTACATCTGGCTATAGTTATATGCACTGGTACC
AACAGAAACCAGGACAGCCACCCAAACTCCTCATCTATCT
TGCATCCAACCTAGAATCTGGGGTCCCTGCCAGGTTCAGT
GGCAGTGGGTCTGGGACAGACTTCACCCTCAACATCCATC
CTGTGGAGGAGGAGGATGCTGCAACCTATTACTGTCAGCA
CAGTAGGGAGCTTCCGTGGACGTTCGGTGGAGGCACCAA
GCTGGAAATCAAA |
| 29 | Heavy Chain | CAGATCCAGTTGGTGCAGTCTGGACCTGAGCTGAAGAAG
CCTGGAGAGACAGTCAAGATCTCCTGCAAGGCTTCTGGTT
ATACCTTCACAGACTATTCAATGCACTGGGTGAAACAGACT
CCAGGAAAGGGTTTAAAGTGGATGGTCTGGATAAACACTG
AGACTGGTGAGCCAACATATGCAGATGACTTCAAGGGACG
GTTTGCCTTCTCTTTGGAAACCTCTGCCAGCACCGCCTATT
TGCAGATCAACAACCTCAAAAATGAGGACACGGCTACATA
TTTCTGTGCTAGAGAGTATGGAAACTACGAGGGGTTTGTT
TACTGGGGCCAAGGGACTCTGGTCACTGTCTCTGCAGCC
AAAACGACACCCCCATCTGTCTATCCACTGGCCCCTGGAT
CTGCTGCCCAAACTAACTCCATGGTGACCCTGGGATGCCT
GGTCAAGGGCTATTTCCCTGAGCCAGTGACAGTGACCTG
GAACTCTGGATCCCTGTCCAGCGGTGTGCACACCTTCCCA
GCTGTCCTGCAGTCTGACCTCTACACTCTGAGCAGCTCAG
TGACTGTCCCCTCCAGCACCTGGCCCAGCGAGACCGTCA
CCTGCAACGTTGCCCACCCGGCCAGCAGCACCAAGGTGG
ACAAGAAAATTGTGCCCAGGGATTGTGGTTGTAAGCCTTG
CATATGTACAGTCCCAGAAGTATCATCTGTCTTCATCTTCC
CCCCAAAGCCCAAGGATGTGCTCACCATTACTCTGACTCC
TAAGGTCACGTGTGTTGTGGTAGACATCAGCAAGGATGAT
CCCGAGGTCCAGTTCAGCTGGTTTGTAGATGATGTGGAGG
TGCACACAGCTCAGACGCAACCCCGGGAGGAGCAGTTCA |

TABLE 4-continued

| SEQ ID NO: | Identity | Sequence |
|---|---|---|
|  |  | ACAGCACTTTCCGCTCAGTCAGTGAACTTCCCATCATGCA<br>CCAGGACTGGCTCAATGGCAAGGAGTTCAAATGCAGGGT<br>CAACAGTGCAGCTTTCCCTGCCCCCATCGAGAAAACCATC<br>TCCAAAACCAAAGGCAGACCGAAGGCTCCACAGGTGTACA<br>CCATTCCACCTCCCAAGGAGCAGATGGCCAAGGATAAAGT<br>CAGTCTGACCTGCATGATAACAGACTTCTTCCCTGAAGAC<br>ATTACTGTGGAGTGGCAGTGGAATGGGCAGCCAGCGGAG<br>AACTACAAGAACACTCAGCCCATCATGGACACAGATGGCT<br>CTTACTTCGTCTACAGCAAGCTCAATGTGCAGAAGAGCAA<br>CTGGGAGGCAGGAAATACTTTCACCTGCTCTGTGTTACAT<br>GAGGGCCTGCACAACCACCATACTGAGAAGAGCCTCTCC<br>CACTCTCCTGGTAAA |
| 30 | Light Chain | GACATTGTGCTGACACAGTCTCCTGCTTCCTTAGCTGTATC<br>TCTGGGGCAGAGGGCCACCATCTCATGCAGGGCCAGCAA<br>AAGTGTCAGTACATCTGGCTATAGTTATATGCACTGGTACC<br>AACAGAAACCAGGACAGCCACCCAAACTCCTCATCTATCT<br>TGCATCCAACCTAGAATCTGGGGTCCCTGCCAGGTTCAGT<br>GGCAGTGGGTCTGGGACAGACTTCACCCTCAACATCCATC<br>CTGTGGAGGAGGAGGATGCTGCAACCTATTACTGTCAGCA<br>CAGTAGGGAGCTTCCGTGGACGTTCGGTGGAGGCACCAA<br>GCTGGAAATCAAACGGGCTGATGCTGCACCAACTGTATCC<br>ATCTTCCCACCATCCAGTGAGCAGTTAACATCTGGAGGTG<br>CCTCAGTCGTGTGCTTCTTGAACAACTTCTACCCCAAAGA<br>CATCAATGTCAAGTGGAAGATTGATGGCAGTGAACGACAA<br>AATGGCGTCCTGAACAGTTGGACTGATCAGGACAGCAAAG<br>ACAGCACCTACAGCATGAGCAGCACCCTCACGTTGACCAA<br>GGACGAGTATGAACGACATAACAGCTATACCTGTGAGGCC<br>ACTCACAAGACATCAACTTCACCCATTGTCAAGAGCTTCAA<br>CAGGAATGAGTGT |

The polynucleotides of the present invention may be in the form of RNA or in the form of DNA, which DNA includes cDNA, and synthetic DNA. The DNA may be double-stranded or single-stranded. The coding sequences that encode the antibodies of the present invention may vary as a result of the redundancy or degeneracy of the genetic code.

The polynucleotides that encode for the antibodies of the present invention may include the following: only the coding sequence for the antibody, the coding sequence for the antibody and an additional coding sequence such as a leader or secretory sequence or a pro-protein sequence; the coding sequence for the antibody and non-coding sequence, such as introns or non-coding sequence 5' and/or 3' of the coding sequence for the protein. Thus, the term "polynucleotide encoding an antibody" encompasses a polynucleotide that may include not only coding sequence for the protein but also a polynucleotide that includes additional coding and/or non-coding sequence.

The polynucleotides of the present invention may be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The present invention also provides recombinant host cells comprising DNA molecules comprising a polynucleotide sequence encoding of comprising a polynucleotide sequence encoding the antibodies of the present invention.

In some embodiments, a recombinant host cell comprises a DNA molecules comprising a polynucleotide sequence encoding a light chain polypeptide having the amino acid sequence SEQ ID NO: 12 and comprising a polynucleotide sequence encoding a heavy chain polypeptide having the amino acid sequence SEQ ID NO: 11, which cell is capable of expressing an antibody comprising a heavy chain and a light chain, wherein the amino acid sequence of the heavy chain is SEQ ID NO: 11 and the amino acid sequence of the light chain is SEQ ID NO: 12.

In other embodiments, a recombinant host cell comprises a DNA molecules comprising a polynucleotide sequence encoding a light chain polypeptide having the amino acid sequence SEQ ID NO: 22 and comprising a polynucleotide sequence encoding a heavy chain polypeptide having the amino acid sequence SEQ ID NO: 21, which cell is capable of expressing an antibody comprising a heavy chain and a light chain, wherein the amino acid sequence of the heavy chain is SEQ ID NO: 21 and the amino acid sequence of the light chain is SEQ ID NO: 22.

The antibodies of the present invention may readily be produced in mammalian cells such as, but not limited to, CHO, NS0, HEK293 or COS cells; in bacterial cells such as, but not limited to, *E. coli, Bacillus subtilis*, or *Pseudomonas fluorescence*; or in fungal or yeast cells. The host cells are cultured using techniques well known in the art.

Vectors containing the polynucleotide sequences of interest (e.g., the polynucleotides encoding the polypeptides of the antibodies and expression control sequences) can be transferred into the host cell by well-known methods, which vary depending on the type of cellular host. For example, calcium chloride transformation is commonly utilized for prokaryotic cells, whereas calcium phosphate treatment or electroporation may be used for other cellular hosts.

Various methods of protein purification may be employed and such methods are known in the art and described, for example, in Deutscher, Methods in Enzymology 182: 83-89 (1990) and Scopes, Protein Purification: Principles and Practice, 3rd Edition, Springer, NY (1994).

The present invention also provides processes for producing the antibodies of the present invention.

In some embodiments, a process for producing an antibody that binds to human CHI3L1 comprising a heavy chain and a light chain is provided, wherein the heavy chain comprises amino acid sequence SEQ ID NO: 11 and the light chain comprises the amino acid sequence of SEQ ID NO: 12, said process comprising the steps of: (a) cultivating a recombinant host cell comprising a first polynucleotide sequence encoding the polypeptide sequence given by SEQ ID NO: 11 and a second polynucleotide sequence encoding the polypeptide sequence given by SEQ ID NO: 12, under conditions such that said antibody is expressed; and (b) recovering from said host cell the expressed antibody. In some embodiments, an antibody produced by the process is provided.

In one embodiment of the above-described process, the first polynucleotide sequence encoding the polypeptide sequence given by SEQ ID NO: 11 and the second polynucleotide sequence encoding the polypeptide sequence given by SEQ ID NO: 12 are part of the same nucleic acid molecule.

In an embodiment, the present invention provides an antibody produced by the afore-mentioned process.

In a further embodiment, the antibody produced by the afore-mentioned process has two heavy chains and two light chains, wherein the polypeptide sequence of each heavy chain is given by SEQ ID NO: 11 and the polypeptide sequence of each light chain is given by SEQ ID NO: 12.

In some embodiments, a process for producing an antibody that binds to human CHI3L1 comprising a heavy chain and a light chain is provided, wherein the heavy chain comprises amino acid sequence SEQ ID NO: 21 and the light chain comprises the amino acid sequence of SEQ ID NO: 22, said process comprising the steps of: a) cultivating a recombinant host cell comprising a first polynucleotide sequence encoding the polypeptide sequence given by SEQ ID NO: 21 and a second polynucleotide sequence encoding the polypeptide sequence given by SEQ ID NO: 22, under conditions such that said antibody is expressed; and b) recovering from said host cell the expressed antibody. In some embodiments, an antibody produced by the process is provided.

In one embodiment of the above-described process, the first polynucleotide sequence encoding the polypeptide sequence given by SEQ ID NO: 21 and the second polynucleotide sequence encoding the polypeptide sequence given by SEQ ID NO: 22 are part of the same nucleic acid molecule.

In an embodiment, the present invention provides an antibody produced by the afore-mentioned process.

In a further embodiment, the antibody produced by the afore-mentioned process has two heavy chains and two light chains, wherein the polypeptide sequence of each heavy chain is given by SEQ ID NO: 21 and the polypeptide sequence of each light chain is given by SEQ ID NO: 22.

In embodiment of the present invention, the antibodies disclosed herein, or the nucleic acids encoding the same, are provided in isolated form.

In aspects, the antibodies of the present invention are monoclonal antibodies. "Monoclonal antibody" or "mAb", as used herein, refers to an antibody that is derived from a single copy or clone including, for example, any eukaryotic, prokaryotic, or phage clone, and not the method by which it is produced. Monoclonal antibodies thereof can be produced, for example, by hybridoma technologies, recombinant technologies, phage display technologies, synthetic technologies, e.g., CDR-grafting, or combinations of such or other technologies known in the art.

Diverse antibodies and antibody fragments (e.g., single chain antibodies, Fab and sFAB fragments, F(ab')2, Fd fragments, Fv fragments, scFv, and domain antibody (dAb) fragments) of the presently disclosed antibodies (e.g., AB1 and AB2 as described herein), as well as antibody mimics, may be readily produced by mutation, deletion and/or insertion within the variable and constant region sequences that flank a particular set of CDRs for the instantly disclosed antibodies (e.g., AB1 and AB2, as described herein). Thus, for example, different classes of the presently disclosed antibodies (e.g., AB1 and AB2 as described herein) are possible for a given set of CDRs (e.g., the CDRs for AB1 and AB2, as described herein) by substitution of different heavy chains, whereby, for example, IgG1-4, IgM, IgA1-2, IgD, IgE antibody types and isotypes may be produced. Similarly, artificial antibodies of the presently disclosed antibodies (e.g., AB1 and AB2 as described herein) within the scope of the invention may be produced by embedding a given set of CDRs (e.g., the CDRs for AB1 and AB2, as described herein) within an entirely synthetic framework. As is known in the art, the term "variable" is used herein to describe certain portions of the variable domains that differ in sequence among antibodies and are used in the binding and specificity of each particular antibody for its antigen. However, as is known in the art, the variability is not usually evenly distributed through the variable domains of the antibodies. It is typically concentrated in three segments called complementarity determining regions ("CDRs") or hypervariable regions both in the light chain and the heavy chain variable domains. The more highly conserved portions of the variable domains are called the framework (FR). The variable domains of heavy and light chains each comprise four framework regions, largely adopting a beta-sheet configuration, connected by three CDRs, which form loops connecting, and in some cases forming part of the beta-sheet structure. The CDRs in each chain are held together in close proximity by the FR regions and, with the CDRs from the other chain, contribute to the formation of the antigen binding site of antibodies (E. A. Kabat et al. Sequences of Proteins of Immunological Interest, fifth edition, 1991, NIH). The constant domains are not involved directly in binding an antibody to an antigen, but exhibit various effector functions, such as participation of the antibody in antibody-dependent cellular toxicity.

The present invention also includes functional equivalents of the antibodies described in this specification (e.g., AB1 and AB2 as described herein). Functional equivalents have binding characteristics that are comparable to those of the antibodies, and include, for example, chimerized, humanized, and single chain antibodies as well as fragments thereof. Methods of producing such functional equivalents are disclosed in PCT Application WO 93/21319, European Patent Application No. 239,400; PCT Application WO 89/09622; European Patent Application 338,745; and European Patent Application EP 332,424, which are incorporated in their respective entireties by reference. In aspects, functional equivalents further include polypeptides with amino acid sequences substantially the same as the amino acid sequence of the variable or hypervariable regions (termed "complementarity determining regions" ("CDR") of the antibodies of the invention. "Substantially the same" as applied to an amino acid sequence is defined herein as a sequence with at least about 90%, 91%, 92%, 94%, 95%, 96%, 97%, 98%, 99%, or any value or range there between, sequence identity to another amino acid sequence, as determined by, e.g., the FASTA search method in accordance with Pearson and Lipman, Proc. Natl. Acad. Sci. USA 85, 2444-2448 (1988).

Chimeric antibodies are immunoglobin molecules characterized by two or more segments or portions derived from different animal species. Chimerized antibodies of the presently disclosed antibodies (e.g., AB1 and AB2 as described herein), preferably have constant regions derived substantially or exclusively from human antibody constant regions and variable regions derived substantially or exclusively from the sequence of the variable region of the instantly disclosed antibodies (e.g., AB1 and AB2 as described herein). Humanized forms of the antibodies are made by substituting the complementarity determining regions of, for example, the presently disclosed antibodies (e.g., AB1 and AB2 as described herein), into a human framework domain, e.g., see PCT Pub. No. WO92/22653. Humanized antibodies preferably have constant regions and variable regions other than the complementarity determining regions (CDRs) derived substantially or exclusively from the corresponding human antibody regions and CDRs derived substantially or exclusively from a mammal other than a human.

Humanized antibodies of the presently disclosed antibodies (e.g., AB1 and AB2 as described herein), may be produced using several technologies such as resurfacing and CDR grafting. In the resurfacing technology, molecular modeling, statistical analysis and mutagenesis are combined to adjust the non-CDR surfaces of variable regions to resemble the surfaces of known antibodies of the target host. Strategies and methods for the resurfacing of antibodies, and other methods for reducing immunogenicity of antibodies within a different host are known in the art, and are disclosed, e.g., in U.S. Pat. No. 5,639,641, which is hereby incorporated in its entirety by reference. In the CDR grafting technology, the murine heavy and light chain CDRs (e.g., the heavy and light chain CDRs for AB1 and AB2, as described herein) are grafted into a fully human framework sequence.

Functional equivalents also include single-chain antibody fragments, also known as single-chain antibodies (scFvs). These fragments contain at least one fragment of an antibody variable heavy-chain amino acid sequence (VH) tethered to at least one fragment of an antibody variable light-chain sequence (VL) with or without one or more interconnecting linkers. Such a linker may be a short, flexible peptide selected to assure that the proper three-dimensional folding of the (VL) and (VH) domains occurs once they are linked so as to maintain the target molecule binding-specificity of the whole antibody from which the single-chain antibody fragment is derived. Generally, the carboxyl terminus of the (VL) or (VH) sequence may be covalently linked by such a peptide linker to the amino acid terminus of a complementary (VL) and (VH) sequence. Single-chain antibody fragments may be generated by molecular cloning, antibody phage display library or similar techniques. These proteins may be produced either in eukaryotic cells or prokaryotic cells, including bacteria.

Single-chain antibody fragments contain amino acid sequences having at least one of the variable or complementarity determining regions (CDRs) of the whole antibodies described in this specification, but are lacking some or all of the constant domains of those antibodies. These constant domains are not necessary for antigen binding, but constitute a major portion of the structure of whole antibodies. Single-chain antibody fragments may therefore overcome some of the problems associated with the use of antibodies containing a part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than whole antibodies.

Functional equivalents further include fragments of antibodies that have the same, or comparable binding characteristics to those of the whole antibody. Such fragments may contain one or both Fab fragments or the F(ab')2 fragment, and can further include sFab fragments, Fd fragments, Fv fragments, and domain antibody (dAb) fragments. In aspects, the antibody fragments contain all six complementarity determining regions of the whole antibody, although fragments containing fewer than all of such regions, such as three, four or five CDRs, are also functional. Further, the functional equivalents may be or may combine members of any one of the following immunoglobulin classes: IgG, IgM, IgA, IgD, or IgE, and the subclasses thereof.

In aspects, the present invention further provides conjugates of the antibodies disclosed herein (e.g., AB1 and AB2 as disclosed herein, including functional equivalents thereof). For example, the antibodies may be covalently attached to a therapeutic agent (e.g., but not limited to a cytotoxic drug, an anti-tumor agent or an immune-oncology agent) either directly or via a cleavable or non-cleavable linker, to an antibody or functional equivalent of the present invention. Non-limiting examples of a cytotoxic drug include methotrexate, daunorubicin, doxorubicin, vincristine, vinblastine, melphalan, mitomycin C, chlorambucil, and calicheamicin. Non-limiting examples of anti-tumor agents include ramucirumab, necitumumab, olaratumab, galunisertib, abemaciclib, cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), and cetuximab. Non-limiting examples of immuno-oncology agents include nivolumab, ipilimumab, pidilizumab, pembrolizumab, tremelimumab, urelumab, lirilumab, atezolizumab, and durvalumab.

In some embodiments, the antibodies disclosed herein (e.g., AB1 and AB2 as disclosed herein, including functional equivalents thereof) are detectably labeled or capable of generating a detectable signal. Such antibodies of the present invention are particularly suitable for diagnostic applications and in vivo imaging. Detectable labels can comprise, for example, a light-absorbing dye, a fluorescent dye, or a radioactive label. Detectable labels, methods of detecting them, and methods of incorporating them into reagents (e.g., antibodies and nucleic acid probes) are well known in the art.

In some embodiments, detectable labels can include labels that can be detected by spectroscopic, photochemical, biochemical, immunochemical, electromagnetic, radiochemical, or chemical means, such as fluorescence, chemifluorescence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies).

The detectable label can be linked by covalent or non-covalent means to the antibodies disclosed herein. Alternatively, a detectable label can be linked such as by directly labeling a molecule that achieves binding to the antibodies disclosed herein via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is labeled with a fluorescent compound. When the fluorescently labeled reagent is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthalaldehyde, fluorescamine, Cy3™, Cy5™, allophycocyanine, Texas Red, peridenin chlorophyll, cyanine, tandem conjugates such as phycoerythrin-Cy5™ green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4',7',4,7-hexachlorofiuorescein (HEX), 6-carboxy-4',5'-dichloro-2',7'-dimethoxyfiuorescein (JOE or J), N,N,N',N'-tetramethyl-6carboxyrhodamine (TAM RA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g., Cy3, Cy5 and Cy7 dyes; coumarins, e.g., umbelliferone; benzimide dyes, e.g., Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc.; BODIPY dyes and quinoline dyes. In some embodiments, a detectable label can be a radiolabel including, but not limited to $^{3}H$, $^{125}I$, $^{35}S$, $^{14}C$, $^{32}P$, and $^{33}P$. In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label the antibodies disclosed herein include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments, a detectable label is a chemiluminescent label, including, but not limited to lucigenin, luminol, luciferin, isoluminol, theromatic acridinium ester, imidazole, acridinium salt and oxalate ester. In some embodiments, a detectable label can be a spectral colorimetric label including, but not limited to colloidal gold or colored glass or plastic (e.g., polystyrene, polypropylene, and latex) beads.

In some embodiments, the antibodies disclosed herein (e.g., AB1 and AB2 as disclosed herein, including functional equivalents thereof) can also be labeled with a detectable tag, such as c-Myc, HA, VSV-G, HSV, FLAG, V5, HIS, or biotin. Other detection systems can also be used, for example, a biotin-streptavidin system. In this system, the antibodies disclosed herein can be biotinylated. Quantity of biotinylated antibody bound to the biomarker is determined using a streptavidin-peroxidase conjugate and a chromogenic substrate. Such streptavidin peroxidase detection kits are commercially available, e.g., from DAKO; Carpinteria, Calif. The antibodies disclosed herein can also be detectably labeled using fluorescence emitting metals such as 152Eu, or others of the lanthanide series. These metals can be attached to the antibodies disclosed herein using such metal chelating groups as diethylenetriaminepentaacetic acid (DTPA) or ethylenediaminetetraacetic acid (EDTA).

The present invention further provides pharmaceutical compositions comprising at least one antibody of the instant disclosure (e.g., AB1 and AB2 as disclosed herein, including functional equivalents thereof) and one or more pharmaceutically acceptable carriers, and/or diluents. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The pharmaceutical compositions can be specially formulated for administration in solid, liquid or gel form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, the compounds described herein can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquids such as suspensions (e.g., aqueous or non-aqueous liquid suspensions, oil-in-water emulsions, or water-in-oil liquid emulsions), solutions, and elixirs; and sterile solids (e.g., crystalline or amorphous solids) that can be reconstituted to provide liquid dosage forms.

Parenteral dosage forms can be administered to patients by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of the antibodies of the present disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

The pharmaceutical compositions may be administered in any dose or dosing regimen. With respect to the therapeutic methods of the invention, it is not intended that the administration be limited to a particular mode of administration, dosage, or frequency of dosing.

The pharmaceutical compositions of the present invention can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

In one embodiment, it may be desirable to administer the pharmaceutical compositions locally to the area in need of treatment; this may be achieved, for example, and not by way of limitation, by local infusion during surgery, topical application, e.g., by injection, by means of a catheter (e.g., a cardiac catheter, renal catheter, intrahepatic catheter, etc.), or by means of an implant, the implant being of a porous, non-porous, or gelatinous material, including membranes, such as silastic membranes, fibers, or commercial skin substitutes. In some embodiments, for certain soft-tissue calcification site accessible by injection, an injection into the calcification site or its vicinity can be desirable.

In some embodiments, the pharmaceutical compositions can be administered to a subject orally (e.g., in capsules, suspensions or tablets) or by parenteral administration. Conventional methods for oral administration include any one of the following; tablets, suspensions, solutions, emulsions, capsules, powders, syrups and the like are usable.

Parenteral administration can include, for example, intramuscular, intravenous, intraarticular, intraarterial, intrathecal, subcutaneous, or intraperitoneal administration. The pharmaceutical composition can also be administered orally, transdermally, topically, by inhalation (e.g., intrabronchial, intranasal, oral inhalation or intranasal drops) or rectally.

When administering the pharmaceutical composition parenterally, it will generally be formulated in a unit dosage injectable form (e.g., solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (e.g., glycerol, propylene glycol, and liquid polyethylene glycol), suitable mixtures thereof, and vegetable oils. The term "Dosage unit" form as used herein refers to physically discrete units suited as unitary dosages for the subjects to be treated; each unit containing a predetermined quantity of active compound calculated to produce the desired therapeutic effect in association with the required pharmaceutical carrier.

An effective amount, e.g., a therapeutically effective dose of the antibodies disclosed herein (e.g., AB1 and AB2 as disclosed herein, including functional equivalents thereof), may be administered to the patient in a single dose or in multiple doses. When multiple doses are administered, the doses may be separated from one another by, for example, one hour, three hours, six hours, eight hours, one day, two days, one week, two weeks, or one month. For example, a composition comprising the compound disclosed herein can be administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

In some embodiments, an effective amount of the pharmaceutical compositions disclosed herein can be an amount which causes the level of CHI3L1 expression to decrease, stabilize, or, at least, to increase at a lower rate than it would be expected to increase in a subject not receiving the pharmaceutical composition. In some embodiments, an effective amount can be an amount that decreases the amount of CHI3L1 polypeptide present in the subject by a statistically significant amount. In some embodiments, an effective amount of the pharmaceutical compositions disclosed herein can be an amount which reduces the activity of CHI3L1 polypeptide. In some embodiments, an effective amount of a CHI3L1 inhibitor can be an amount which lowers the NAI by at least 5%, at least 10%, at least 20%, at least 30%, at least 40%, at least 50%, at least 60%, at least 70%, at least 80%, or at least 90%.

A physician may, for example, prescribe a relatively low dose at first, subsequently increasing the dose until an appropriate response is obtained. The dose administered to a patient is sufficient to affect a beneficial therapeutic response in the patient over time, or, e.g., to reduce symptoms, or other appropriate activity, depending on the application. The dose is determined by the efficacy of the particular formulation, and the activity, stability or serum half-life of the composition being administered, and the condition of the patient, the particular condition of soft-tissue calcification to be treated, as well as the body weight or body surface area. The size of the dose is also determined by the existence, nature, and extent of any adverse side-effects that accompany the administration of a particular formulation, or the like in a particular subject. Therapeutic compositions are optionally tested in one or more appropriate in vitro and/or in vivo animal models of disease, and known to persons of ordinary skill in the art, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the $LD_{50}$ of the relevant formulation, and/or observation of any side-effects of the pharmaceutical composition at various concentrations, e.g., as applied to the mass and overall health of the patient.

The dosage can be determined by one of skill in the art and can also be adjusted by the individual physician in the event of any complication. Typically, the dosage of a composition comprising the antibodies disclosed herein can range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, or from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, or from 4.5 g/kg body weight to 5 g/kg body weight. Effective doses may be extrapolated from dose-response curves derived from in vitro or animal model test bioassays or systems. The dosage should not be so large as to cause unacceptable adverse side effects.

In some embodiments, a method of treating NAFLD and/or NASH in a subject is provided, the method comprising administering a therapeutically-effective amount of at least one antibody that binds to human CHI3L1 of the instant disclosure (e.g., AB1 and AB2 as disclosed herein, including functional equivalents thereof) to the subject. In some aspects, a method of treating liver cirrhosis in a subject is provided, the method comprising administering a therapeutically-effective amount of at least one antibody that binds to human CHI3L1 of the instant disclosure to the subject. In some aspects, a method of treating HCC in a subject is provided, the method comprising administering a therapeutically-effective amount of at least one antibody that binds to human CHI3L1 of the instant disclosure to the subject.

In a further embodiment of the methods for treating NAFLD and/or NASH, liver cirrhosis, and/or HCC, the methods comprise the administration of an effective amount of at least one antibody of the instant disclosure (e.g., AB1 and AB2 as disclosed herein, including functional equivalents thereof) in simultaneous, separate, or sequential combination with one or more cytotoxic agents, anti-tumor agents, or immune-oncology agents, as previously described.

In some embodiments, the antibodies disclosed herein (e.g., AB1 and AB2 as disclosed herein, including functional equivalents thereof) may be used in various assays and techniques, including immunoassays. Such assays and techniques include, but are not limited to, competitive and non-competitive assay systems using techniques such as Western blots, radioimmunoassay (RIA), ELISA (enzyme linked immunosorbent assay), "sandwich" immunoassays, immunoprecipitation assays, immunodiffusion assays, agglutination assays, e.g., latex agglutination, complement-fixation assays, immunoradiometric assays, fluorescent immunoassays, e.g., FIA (fluorescence-linked immunoassay), chemiluminescence immunoassays (CLIA), electro-chemiluminescence immunoassay (ECLIA, counting immunoassay (CIA), lateral flow tests or immunoassay (LFIA), magnetic immunoassay (MIA), protein A immunoassays, immunohistochemistry techniques, immunocytochemistry techniques, electrophoresis techniques (including SDS-PAGE electrophoresis, 2D SDS-PAGE electrophoresis. Methods for performing such assays are known in the art. In some embodiments, the immunoassay can be a quantitative or a semi-quantitative immunoassay, immunohistochemistry techniques, immunocytochemistry techniques, electrophoresis techniques (including SDS-PAGE electrophoresis, 2D SDS-PAGE electrophoresis.

In various embodiments, using the antibodies of the instant disclosure (e.g., AB1 and AB2 as disclosed herein, including functional equivalents thereof), a highly-specific two-site monoclonal based immunoassay that can clearly distinguish between healthy subjects and diseased subjects, such as those suffering from NAFLD/NASH as well as liver cirrhosis and/or HCC is disclosed.

In various embodiments an assay is provided, the assay comprising: (i) measuring, in a sample obtained from a subject, a level of CHI3L1, wherein said measuring comprises incubating the sample with at least one antibody of the instant disclosure (e.g., AB1 and AB2 as disclosed herein, including functional equivalents thereof); (ii) comparing the level of CHI3L1 with a reference level; and (iii) identifying the subject as (a) having NAFLD or NASH if the level of CHI3L1 is above the reference level; or (b) not having NAFLD or NASH if the level of CHI3L1 is at or below the reference level. In some aspects, incubating the sample with at least one antibody of the instant disclosure comprises incubating the sample with an antibody in an article with an immobilized antibody of any one of claims 1-4. In some aspects, the reference level is about 2.0 ng/30 μL serum. In some aspects, when the level of CHI3L1 is above the reference level, the assay further comprises providing a treatment appropriate for treating NAFLD or NASH. In some aspects, the treatment comprises administering a CHI3L1 inhibitor. In some aspects, the CHI3L1 inhibitor comprises at least one antibody that binds to human CHI3L1 of the instant disclosure (e.g., AB1 and AB2 as disclosed herein, including functional equivalents thereof).

In various embodiments, as assay is provided, the assay comprising: (i) measuring, in a sample obtained from a subject, a level of CHI3L1, wherein said measuring comprises incubating the sample with at least one antibody of the instant disclosure (e.g., AB1 and AB2 as disclosed herein, including functional equivalents thereof); (ii) comparing the level of CHI3L1 with a reference level; and (iii) identifying the subject as (a) having liver cirrhosis if the level of CHI3L1 is above the reference level; or (b) not having liver cirrhosis if the level of CHI3L1 is at or below the reference level. In some aspects, incubating the sample with at least one antibody of the instant disclosure comprises incubating the sample with an antibody in an article with an immobilized antibody of any one of claims 1-4. In some aspects, the reference level is about 60 ng/mL, about 61 ng/mL, about 62 ng/mL, about 63 ng/mL, about 64 ng/mL, about 65 ng/mL, about 66 ng/mL, about 67 ng/mL, about 68 ng/mL, about 69 ng/mL, about 70 ng/mL, about 71 ng/mL, about 72 ng/mL, about 73 ng/mL, about 74 ng/mL, about 75 ng/mL, or any value or range there between. In some aspects, the reference level is about 2.0 ng/30 µL. In some aspects, when the level of CHI3L1 is above the reference level, the assay further comprises providing a treatment appropriate for treating liver cirrhosis. In some aspects, the treatment comprises administering a CHI3L1 inhibitor. In some aspects, the CHI3L1 inhibitor comprises at least one antibody that binds to human CHI3L1 of the instant disclosure (e.g., AB1 and AB2 as disclosed herein, including functional equivalents thereof).

In some embodiments, an assay is provided, the assay comprising: (i) measuring, in a sample obtained from a subject, a level of CHI3L1, wherein said measuring comprises incubating the sample with at least one antibody of the instant disclosure (e.g., AB1 and AB2 as disclosed herein, including functional equivalents thereof); (ii) comparing the level of CHI3L1 with a reference level; and (iii) identifying the subject as (a) having HCC if the level of CHI3L1 is above the reference level; or (b) not having HCC if the level of CHI3L1 is at or below the reference level. In some aspects, incubating the sample with at least one antibody of the instant disclosure comprises incubating the sample with an antibody in an article with an immobilized antibody of any one of claims 1-4. In some aspects, the reference level is about 2 ng/30 µL. In some aspects, when the level of CHI3L1 is above the reference level, the assay further comprises providing a treatment appropriate for treating HCC. In some aspects, the treatment comprises administering a CHI3L1 inhibitor. In some aspects, the CHI3L1 inhibitor comprises at least one antibody that binds to human CHI3L1 of the instant disclosure (e.g., AB1 and AB2 as disclosed herein, including functional equivalents thereof).

In some embodiments, a method of monitoring treatment progress in a subject having NAFLD or NASH is provided, the method comprising: (i) measuring, at a first time point, a first level of CHI3L1 in a first sample obtained from the subject, wherein said measuring comprises incubating the sample with at least one antibody of the instant disclosure (e.g., AB1 and AB2 as disclosed herein, including functional equivalents thereof); (ii) administering to the subject a therapeutic agent for treating NAFLD or NASH; and (iii) measuring, at a second time point, a second level of CHI3L1 in a second sample obtained from the subject, wherein said measuring comprises incubating the sample with at least one antibody of the instant disclosure (e.g., AB1 and AB2 as disclosed herein, including functional equivalents thereof)/incubating the sample with an antibody in an article with an immobilized antibody of any one of claims 1-4, wherein the second time point is later than the first time point and after said administering, and wherein if the second level is significantly lower than the first level, then the treatment is considered to be effective. In some aspects, measuring a first level of CHI3L1 at a first time point and/or measuring a second level of CHI3L1 at a second time point comprises incubating the sample with an antibody in an article with an immobilized antibody of any one of claims 1-4. In some aspects, the therapeutic agent is a CHI3L1 inhibitor. In some aspects, the CHI3L1 inhibitor comprises at least one antibody that binds to human CHI3L1 of the instant disclosure (e.g., AB1 and AB2 as disclosed herein, including functional equivalents thereof). It should be understood that the above method could also be used to not only monitor the treatment progress in a subject having NAFLD and/or NASH in a subject, but also subsequent complications of untreated progression in the liver of a subject, such as liver cirrhosis and/or HCC.

The present invention further provides kits for performing any of the method and/or assays described herein, including diagnosis and/or treatment of NAFLD and/or NASH (as well as subsequent complications of untreated progression in the liver of a subject, such as liver cirrhosis and/or HCC). In some embodiments, the kit can comprise at least one antibody of the instant disclosure (e.g., AB1 and AB2 as disclosed herein, including functional equivalents thereof). A kit is any manufacture (e.g., a package or container) comprising at least one antibody of the instant disclosure (e.g., AB1 and AB2 as disclosed herein, including functional equivalents thereof) for specifically detecting, e.g., a CHI3L1 expression product or fragment thereof, the manufacture being promoted, distributed, or sold as a unit for performing the methods or assays described herein.

In some embodiments, described herein is a kit for the detection of a CHI3L1 expression product in a sample, the kit comprising at least one antibody of the instant disclosure (e.g., AB1 and AB2 as disclosed herein, including functional equivalents thereof) which specifically binds to the CHI3L1 expression product, on a solid support. The at least one antibody of the instant disclosure can optionally comprise a detectable label. The kits described herein include reagents and/or components that permit assaying the level of a CHI3L1 expression product in a sample obtained from a subject (e.g., a biological sample obtained from a subject). The kits described herein can optionally comprise additional components useful for performing the methods and assays described herein.

A kit can further comprise devices and/or reagents for concentrating an expression product (e.g., a polypeptide) in a sample, e.g., a serum sample. Thus, ultrafiltration devices permitting, e.g., protein concentration can also be included as a kit component.

Preferably, a diagnostic or prognostic kit for use with the methods and assays disclosed herein contains detection reagents for CHI3L1 expression products. Such detection reagents comprise, in addition to at least one antibody of the instant disclosure (e.g., AB1 and AB2 as disclosed herein, including functional equivalents thereof) and possibly other CHI3L1-specific reagents, for example, buffer solutions, labels or washing liquids etc. Furthermore, the kit can comprise an amount of a known nucleic acid and/or polypeptide, which can be used for a calibration of the kit or as an internal control. A diagnostic kit for the detection of an expression product can also comprise accessory ingredients like secondary affinity ligands, e.g., secondary antibodies, detection dyes and any other suitable compound or liquid necessary for the performance of an expression product detection method known to the person skilled in the art. Such ingredients are known to the person skilled in the art and may vary depending on the detection method carried out. Additionally, the kit may comprise an instruction leaflet and/or may provide information as to the relevance of the obtained results.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

EXAMPLES

The invention now being generally described, it will be more readily understood by reference to the following examples which are included merely for purposes of illustration of certain aspects and embodiments of the present invention, and are not intended to limit the invention.

Example 1 Production of Monoclonal Antibodies to CH3L1

The cDNA encoding for the CHI3L1 protein was cloned into an expression vector with a HIS-tag and transfected into bacteria. Cellular lysates were prepared, clarified and the human CHI3L1 protein purified on a nickel (Ni) column as shown in FIG. 1. The CHI3L1 protein was purified following elution with PBS and the HIS-tag removed by enzymatic digestion. The final purified CHI3L1 protein was used to immunize mice. This protein is not immunogenic and required multiple immunizations at various concentrations with complete and incomplete Freud's adjuvant to produce several IgG and IgM anti-CHI3L1 monoclonal antibodies. The preferred immunization method was to primarily immunize the mice intraperitoneally (IP) with 10 μg of recombinant CHI3L1 protein in 50% normal saline and 50% complete Freund's adjuvant in a total injected volume of 0.5 ml. At least six weeks later, mice received an IP booster immunization of 10 μg CHI3L1 protein in 50% saline and 50% incomplete Freund's adjuvant in a total volume of 250 μL. Three days before the fusion procedure, the mice received another intravenous boost with 10 μg of CHI3L1 protein in normal saline in a total volume of 100 μL. The preferred fusion procedure is as follows: mice are euthanized and the spleen is removed. The spleen is dissociated with needles into Dulbecco's Modified Eagle Medium (DMEM) and the cells in suspension are collected. The second cell line is Sp2/0-Ag14 mouse myeloma cells that grow in suspension in DMEM with 20% fetal bovine serum. Completely confluent cells growing in a 20 mm×10 cm dish are harvested. After three individual washes, the two cell suspensions are combined. After spinning at 1000 rpm for 5 minutes at room temperature, the pellet cells are fused with 1 mL of 60% polyethylene glycol for 6 minutes at 37° C. After fusion, cells are plated and then selected with HAT (hypoxanthine, aminopterin, and thymidine) medium. Cells that survive the selection are tested for the presence of antibody using an ELISA assay which employs a 96-well plate coated with CHI3L1 protein. Clones positive for this antibody are maintained and dilutionally cloned. After cloning, positive cell lines/hybridomas are maintained, characterized, and ultimately preserved in liquid nitrogen. The hybridomas are cloned ×2 (twice) and injected into pristine primed BALB-c mice to produce ascites (abnormal accumulation fluid in the abdominal cavity) as previously described (Nambotin, S. B., et al. Functional consequences of WNT3/Frizzled7-mediated signaling in non-transformed hepatic cells. *Oncogenesis* 1, e31 (2012), herein incorporated by reference in its entirety).

The growth and purification of antibodies are as follows: cell lines determined to be secreting an antibody of interest are expanded, and the corresponding antibody is generated via the ascites method. Mice are injected intraperitoneally with 0.5 mL of pristane. After 7 days, four million hybridoma cells in 0.5 mL DMEM are intraperitoneally injected. After approximately 10 days the mice are euthanized and the ascites fluid is collected from the abdomen, spun for 5 minutes at 1000 rpm at room temperature, and the supernatant containing the antibody is collected. The antibodies are isotyped using a commercial kit. IgGs of interest are purified from ascites using a HiTrap protein G column. Ascites fluid is diluted at 1:20 in loading buffer, filtered with 0.45 μm MCE (mixed cellulose ester) membrane, and then loaded onto the column at neutral pH. The antibodies are eluted at acid pH, immediately neutralized and then dialyzed against 2× normal saline. The protein concentration is determined via a BCA assay, the level of purity by PAGE gel electrophoresis.

Example 2 Sequencing of the Monoclonal Antibodies to CH3L1

Total RNA was isolated from the hybridoma cells (described in Example 1) following the technical manual of TRIzol® Reagent (Ambion, Cat. No.: 15596-026). Total RNA was then reverse-transcribed into cDNA using either isotype-specific anti-sense primers or universal primers following the technical manual of PrimeScript™ 1st Strand cDNA Synthesis Kit (Takara, Cat. No.: 6110A). Antibody fragments of $V_H$, $V_L$, $C_H$ and $C_L$ were amplified according to the standard operating procedure (SOP) of rapid amplification of cDNA ends (RACE) of GenScript. Amplified antibody fragments were cloned into a standard cloning vector separately. Colony PCR was performed to screen for clones with inserts of correct sizes. No less than five colonies with inserts of correct sizes were sequenced for each fragment. The sequences of different clones were aligned and the consensus sequence was provided.

Example 3 Establishment of an ELISA Assay for Serum Detection

Figure 2:
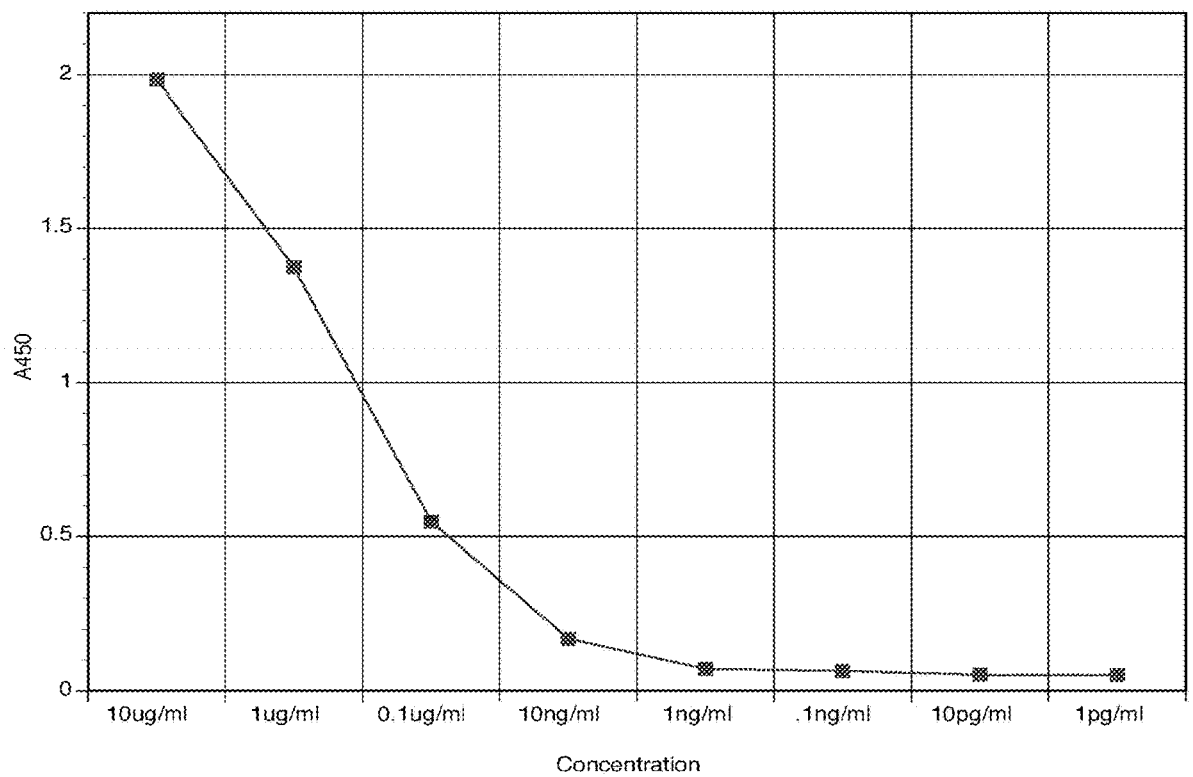
FIG. 2 demonstrates that monoclonal AB1 (CH568) binds to CHI3L1 protein when coated on the plate, which can be detected at a concentration of approximately 2 ng/mL.
Figure 3:
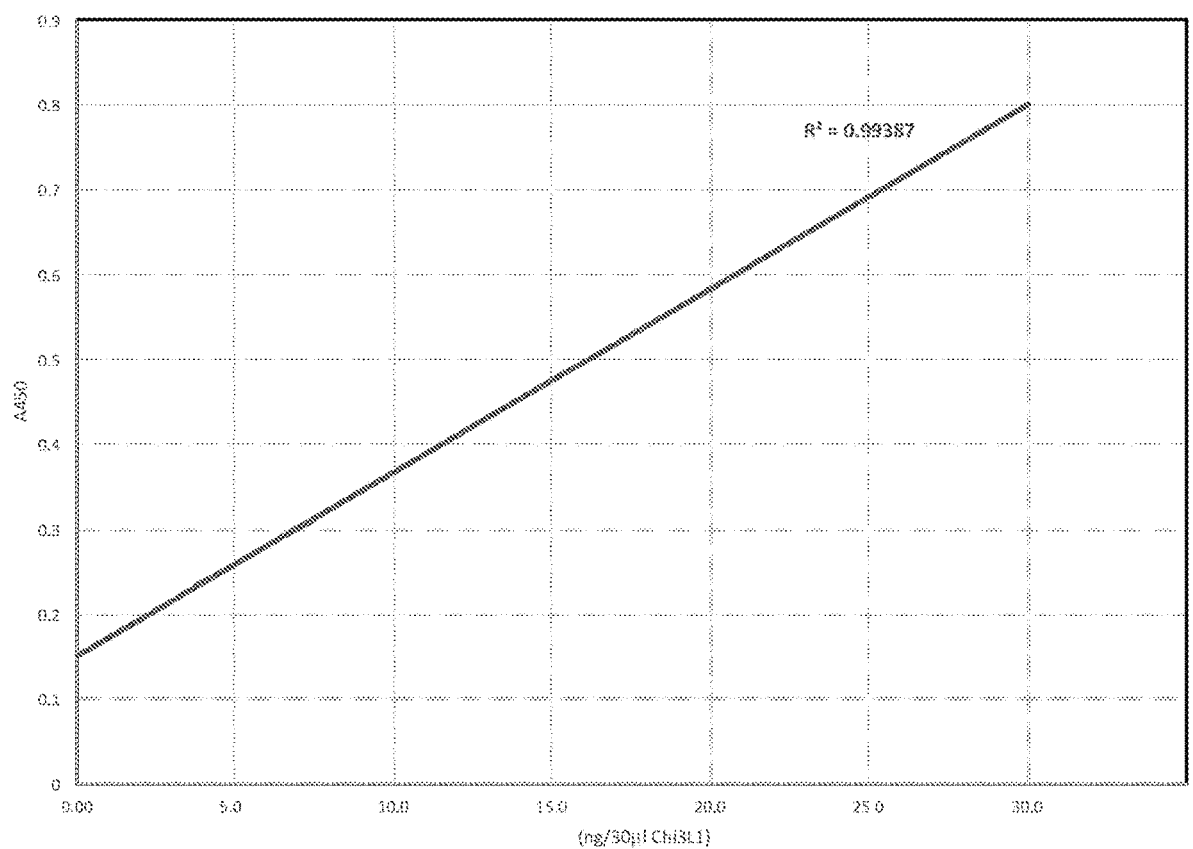
FIG. 3 demonstrates the performance of a two-site monoclonal antibody-based ELISA using the antibodies disclosed herein with respect to binding to the recombinant CHI3L1 protein in a standard curve. Note that the binding activity is linear over a wide concentration range of 2-50 ng/30 µL of CHI3L1 protein. This standard curve is used to determine the level of CHI3L1 protein in the blood in individuals with NAFLD/NASH (as shown in Table 5) and normal controls (as shown in Table 6).

Purified immunoglobulins are then stored at −80° C. prior to any application following the characterization of their immunoreactivity towards CHI3L1 protein in an ELISA assay format as shown in FIG. 2. The IgG and IgM antibodies are tested for performance in a 2-site assay. AB1 (also referred to as "CH568") is bound to a solid phase support (96-well polystyrene plate) and the detecting antibody, AB2 (also referred to as "CHXi3b-6") is biotin labeled using standard and well established procedures, which enables 6 molecules of biotin to link to one molecule of AB2. The operational characteristic of this 2-site mAb-based assay (each antibody recognizes a distinct and separate epitope on the CHI3L1 protein) is determined with a coefficient variation between assay samples of less than 10%. As shown in FIG. 3, a standard curve constructed from this assay reveals a linear relationship over a concentration range of 2-50 ng/30 μL serum with a $R^2$ value of 0.99387. Detailed methods for assay design and performance are as follows:

Two-Site Monoclonal Antibody-Based Assay for CHI3L1

1. Using a standard high binding immunoassay plate from Corning or Nunc, AB1 (CH568) is coated on the plate at a concentration of 3 μg/mL in 0.2 M sodium carbonate-bicarbonate buffer (pH 9.4). Then 100 μL of antibody solution is applied per well and allowed to sit overnight at room temperature (RT).
2. After coating, the plates are washed twice with Tris Buffered Saline (TBS)+0.05% Tween 20.
3. The plates are incubated at 37° C. with 315 μL of a blocking buffer, TBS+2% w/v Bovine Serum Albumin (BSA) for 2 hours.
4. After blocking, the plates are washed five times and then the samples are loaded. The assay buffer is TBS (pH 7.2)+1% BSA. The standard curve is incubated in assay buffer plus 30% fetal bovine serum. The plate containing the samples is incubated for 2 hours at 37° C.
5. The plates are then washed 5× with washing buffer and a solution of 3 μg/mL biotinylated AB2 (CHXI3B6-6) is incubated for 1.5 hours at 37° C.
6. The plates are washed and then incubated with a 1:5000 dilution of Streptavidin-Peroxidase in TBS/1% BSA for 45 minutes at 37° C.
7. The wells are washed 5× and developed with TMB substrate.

The reaction is terminated after 30 minutes with 2.0 N $H_2SO_4$ and the plate is read on a spectrophotometer at 450 nm.

Example 4 ELISA Assays

Two-Site Monoclonal Antibody-Based ELISA Assays were performed to detect CHI3L1 protein in serum samples derived from normal and NAFLD/NASH individuals, and to evaluate correlations with liver enzyme levels in serum, liver histology, as well as the presence and degree of fibrosis in NASH patients.

After individuals have signed informed consent, their blood and liver biopsy materials are analyzed for alanine aminotransferase (ALT) and aspartate aminotransferase (AST) levels to detect liver damage. Liver biopsy tissue is used to determine the NASH activity score (NAS) as measured by degree of steatosis, grade of inflammation, the presence of ballooning degeneration in hepatocytes, as well as the presence and degree of liver fibrosis as previously described (Promrat, K., et al. Randomized controlled trial testing the effects of weight loss on nonalcoholic steatohepatitis. *Hepatology* 51, 121-129 (2010), herein incorporated by reference in its entirety).

Table 5 demonstrates that both males and females are affected with this disease and almost all individuals are overweight or obese as defined by a BMI greater than 25 or 30, respectively. The level of CHI3L1 in serum ranged from 2.2 to 58.6 ng/30 μL serum sample as measured in 27 individuals with NAFLD/NASH. In addition, 93% of patients (23/25) exhibit evidence for liver damage as measured by elevated ALT and AST levels in blood. The NASH activity score (NAS) ranged from moderate to severe as determined by liver pathology. More important, most positive individuals in this ELISA assay have advanced fibrosis and even cirrhosis as determined by a fibrosis score of 4 or greater. Therefore, this two-site monoclonal antibody based assay is able to identify moderate to severe NASH disease in the liver by quantifying CHI3L1 protein in blood. In contrast, as shown in Table 6, most normal individuals studied do not have detectable CHI3L1 protein in their blood with the notable exception of one individual (#18). It would anticipated that, because of the high prevalence of NAFLD in the U.S.A. general population, some individuals previously considered to be "normal" may have NASH and become reactive in this assay.

Table 5 shows the CHI3L1 levels in serum derived from individuals with NAFLD/NASH.

TABLE 5

| | NAFLD PATIENTS CHI3L1 LEVELS | | | | | |
|---|---|---|---|---|---|---|
| Patient ID | CHI3L1 (ng/30 μL) Normal level <2.0 ng/30 μL serum | CHI3L1 (pg/mL) R&D Systems Assay | NAS | ALT/AST Normal level F: 29/36; M: 32/38 | Gender | BMI |
| 3 | 53.5 | 68881 | 5 | 67/47 | M | 41.6 |
| 16 | 32.4 | 85825 | 5 | 131/70 | M | 31.14 |
| 19 | 40.9 | 116286 | 5 | 57/48 | M | 37.71 |
| 20 | 49.6 | 37268 | 5 | 75/36 | M | 27.14 |
| 26 | 5.6 | 57196 | 7 | 187/162 | F | 33.27 |
| 31 | 40.6 | 106934 | 5 | 122/188 | M | 30.45 |
| 37 | 2.5 | 108727 | 5 | | M | 36.98 |
| 55 | 2.2 | 26767 | 5 | 30/24 | F | 39.44 |
| 58 | 4.9 | 41015 | 3 | 54/122 | F | 25.13 |
| 71 | 39.3 | 159151 | | 83/69 | F | 29.03 |
| 90 | 40.8 | 63991 | 2 | | M | 30.82 |
| 109 | 9.1 | 15477 | 2 | 71/46 | M | 31.78 |
| 111 | 52.1 | 69659 | 6 | 96/95 | M | 37.24 |
| 118 | 42.8 | 70683 | 4 | 111/74 | M | 34.28 |
| 120 | 22.1 | 51731 | 5 | 94/61 | M | 33.36 |
| 123 | 2.4 | 37603 | 5 | 91/66 | F | 35.29 |
| 136 | 11.3 | 30199 | 5 | 90/66 | F | 45.36 |
| 145 | 50.9 | 69730 | 5 | 85/59 | F | 33.6 |
| 151 | 4.5 | 75791 | 2 | 51/53 | F | 28.71 |
| 154 | 5.4 | 113146 | 4 | 119/82 | M | 33.09 |
| 173 | 26.7 | 40820 | 5 | 160/88 | F | 31.32 |
| 176 | 6.1 | 28711 | 3 | 41/38 | M | 33.39 |

TABLE 5-continued

NAFLD PATIENTS CHI3L1 LEVELS

| Patient ID | CHI3L1 (ng/30 µL) Normal level <2.0 ng/30 µL serum | CHI3L1 (pg/mL) R&D Systems Assay | NAS | ALT/AST Normal level F: 29/36; M: 32/38 | Gender | BMI |
|---|---|---|---|---|---|---|
| 182 | 3.5 | 17554 | 4 | 58/37 | M | 31.07 |
| 185 | 22.2 | 178638 | 7 | 120/125 | F | 30.76 |
| 190 | 10.7 | 44533 |   | 68/94 | F | 25.9 |
| 196 | 8.5 | 11238 | 3 |   | M | 29.51 |
| 198 | 58.6 | 41607 | 4 | 37/27 | M | 34.62 |

Table 6 shows CHI3L1 levels in serum derived from normal blood donors and volunteers.

TABLE 6

| Individual ID | CHI3L1 Level (ng/30 µL serum) Normal level <2.0 ng/30 µL | Gender | Age |
|---|---|---|---|
| 1 | <2.0 | F | 32 |
| 2 | <2.0 | F | 21 |
| 3 | <2.0 | F | 47 |
| 4 | <2.0 | M | 53 |
| 5 | <2.0 | M | 62 |
| 6 | <2.0 | M | 69 |
| 7 | <2.0 | F | 37 |
| 8 | <2.0 | M | 41 |
| 9 | <2.0 | M | 39 |
| 10 | <2.0 | M | 27 |
| 11 | <2.0 | M | 62 |
| 12 | <2.0 | F | 55 |
| 13 | <2.0 | F | 49 |
| 14 | <2.0 | M | 42 |
| 15 | <2.0 | F | 34 |
| 16 | <2.0 | F | 57 |
| 17 | <2.0 | M | 61 |
| 18 | 60.2 | M | 46 |
| 19 | <2.0 | M | 43 |
| 20 | <2.0 | F | 52 |
| 21 | <2.0 | M | 58 |
| 22 | <2.0 | F | 62 |
| 23 | <2.0 | M | 39 |
| 24 | <2.0 | M | 47 |
| 25 | <2.0 | M | 63 |

Example 5 CHI3L1 Protein Levels Measured in Clinical Samples

Figure 4:
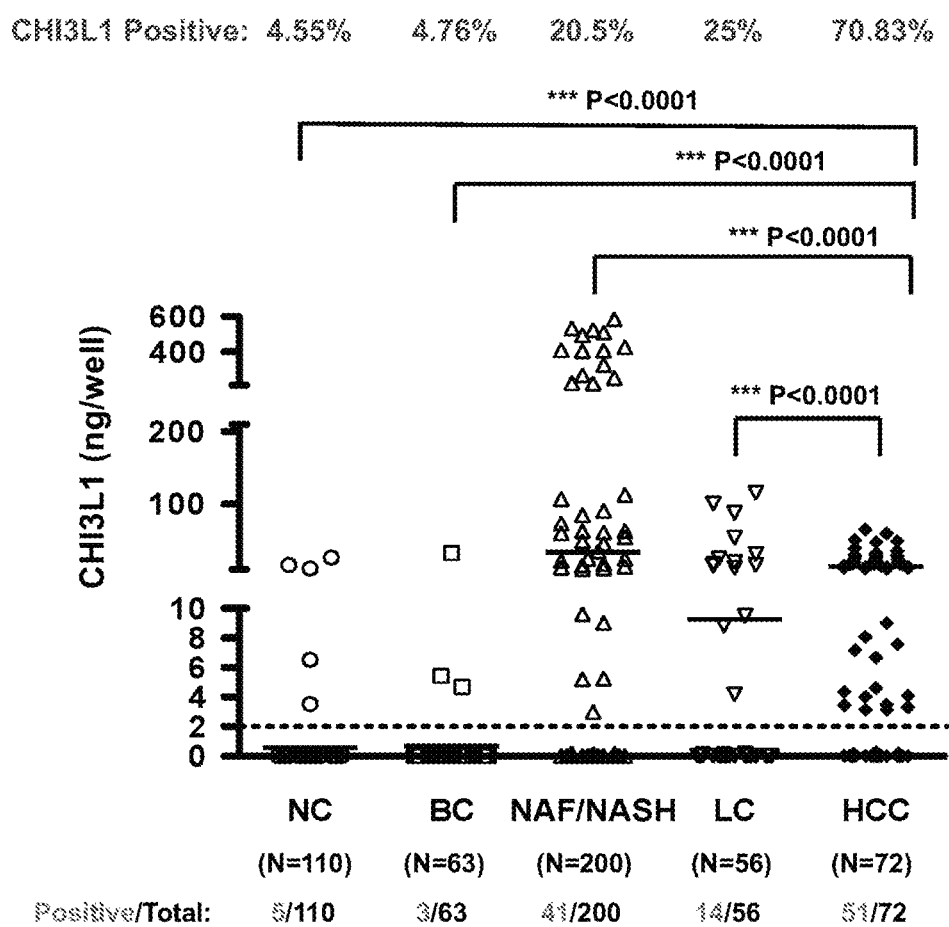
FIG. 4 depicts CHI3L1 protein levels in blood derived from various groups of normal controls (NC), nonalcoholic fatty liver disease/nonalcoholic steatohepatitis (NAFLD/NASH), liver cirrhosis (LC) and hepatocellular carcinoma (HCC) as determined using a two-site monoclonal antibody-based ELISA using the antibodies disclosed herein. Note the group of exceedingly high values in the NAFLD/NASH cohort.
Figure 5:
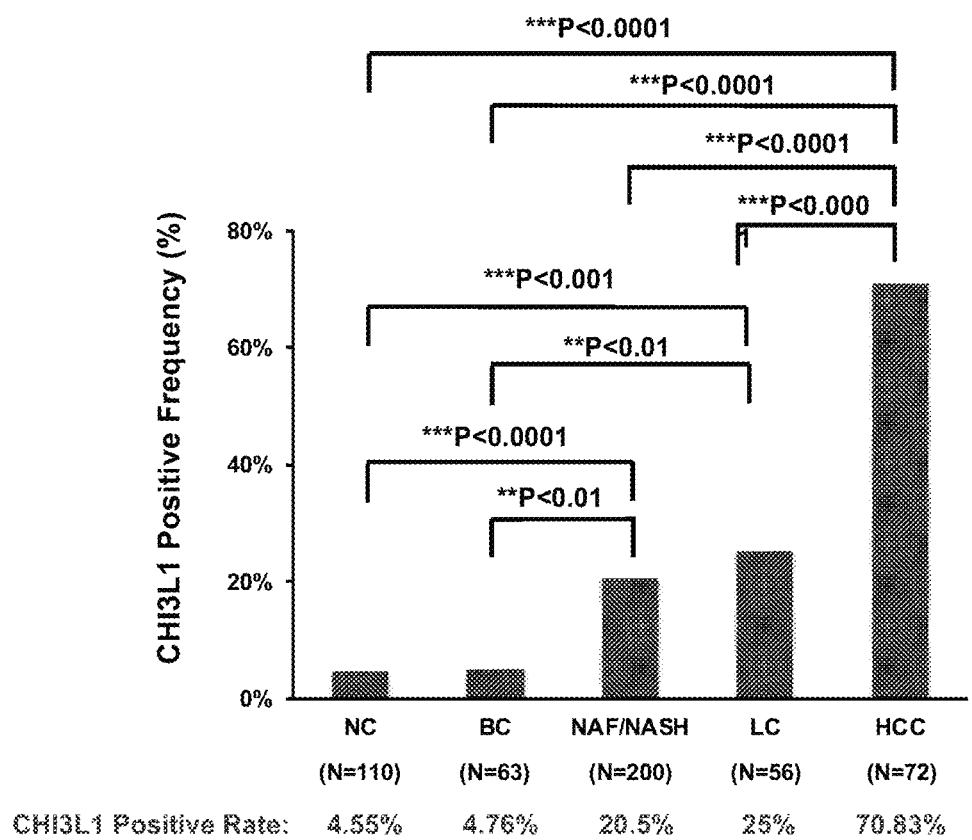
FIG. 5 depicts the comparison of the positive rate between the various clinical groups as determined using a two-site monoclonal antibody-based ELISA using the antibodies disclosed herein, where NC represents normal control, BC represents breast cancer, NAFLD/NASH represents nonalcoholic fatty liver disease/nonalcoholic steatohepatitis, LC represents liver cirrhosis, and HCC represents hepatocellular carcinoma.

This two-site monoclonal antibody-based ELISA assay for detection of CHI3L1 protein was tested in clinical samples derived from normal controls (NC), breast cancer (BC), nonalcoholic fatty liver disease/nonalcoholic steatohepatitis (NAFLD/NASH), liver cirrhosis (LC), and hepatocellular carcinoma (HCC). It is well known that individuals with NASH may progress to LC and HCC, which are the dreaded complications of this progressive liver disease. It was unanticipated that the two-site monoclonal antibody-based assay also detected patients with both LC and HCC indicating a unique tripartite assay that can not only detect the primary disease NAFLD and/or NASH, but also the subsequent complications such as LC and HCC. This finding has not previously been observed in any two-site monoclonal antibody-based assay. In this context, FIG. 4 demonstrates the results of these studies and details the absolute concentration of CHI3L1 protein as measured in ng/well (100 µL). Note the exceedingly high values of this protein in individuals with NASH as compared to the other groups which may indicate that the disease is progressing rapidly in such individuals. In a "normal" population of blood donors, the positive rate was only 4.55%; and the positive rate in breast cancer was similar at 4.76%, which may indicate the background prevalence of NAFLD/NASH in the general population. In contrast, 20.5% of serum samples derived from NASH individuals were highly positive for this protein and 25% of LC individuals were also reactive in the assay. Finally, there was extraordinarily high rate of positivity in HCC of 70.83% (FIG. 5). Therefore, this assay has a unique feature of detecting the primary disease (NAFLD/NASH) and the subsequent complications of untreated progression in the liver (LC and HCC).

All publications and patents mentioned in the above specification are herein incorporated by reference. It will be apparent to those skilled in the art that various modifications and variations can be made to the present inventive technology without departing from the spirit and scope of the disclosure. Although the disclosure has been described in connection with specific preferred embodiments, it should be understood that the disclosure as claimed should not be unduly limited to such specific embodiments. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

What is claimed is:

1. An antibody that binds to human CHI3L1 comprising a light chain and a heavy chain, wherein the light chain comprises a light chain variable region (LCVR) and the heavy chain comprises a heavy chain variable region (HCVR), wherein the LCVR comprises complementarity determining regions LCDR1, LCDR2, and LCDR3, and the HCVR comprises complementarity determining regions HCDR1, HCDR2, and HCDR3, wherein LCDR1 consists of amino acid sequence SEQ ID NO:6, LCDR2 consists of amino acid sequence SEQ ID NO:7, LCDR3 consists of amino acid sequence SEQ ID NO:8, HCDR1 consists of amino acid sequence SEQ ID NO:3, HCDR2 consists of amino acid sequence SEQ ID NO:4, and HCDR3 consists of amino acid sequence SEQ ID NO:5.

2. The antibody of claim 1, wherein the LCVR comprises amino acid sequence SEQ ID NO: 10 and the HCVR comprises amino acid sequence SEQ ID NO: 9.

3. The antibody of claim 1, wherein the light chain comprises amino acid sequence SEQ ID NO: 12 and the heavy chain comprises amino acid sequence SEQ ID NO: 11.

4. The antibody of claim 1, wherein the antibody comprises two light chains and two heavy chains, wherein each light chain comprises amino acid sequence SEQ ID NO: 12 and each heavy chain comprises SEQ ID NO: 11.

5. A DNA molecule comprising a polynucleotide sequence encoding a light chain polypeptide having the amino acid sequence SEQ ID NO: 12.

6. A DNA molecule comprising a polynucleotide sequence encoding a heavy chain polypeptide having the amino acid sequence SEQ ID NO: 11.

7. A pharmaceutical composition comprising an antibody of claim 1 and one or more pharmaceutically acceptable carriers, diluents or excipients.

* * * * *

SEQUENCE LISTING

<160> NUMBER OF SEQ ID NOS: 30

<210> SEQ ID NO 1
<211> LENGTH: 383
<212> TYPE: PRT
<213> ORGANISM: Homo sapiens

<400> SEQUENCE: 1

Met Gly Val Lys Ala Ser Gln Thr Gly Phe Val Val Leu Val Leu Leu

```
1               5                    10                   15
Gln Cys Cys Ser Ala Tyr Lys Leu Val Cys Tyr Tyr Thr Ser Trp Ser
                20                  25                  30
Gln Tyr Arg Glu Gly Asp Gly Ser Cys Phe Pro Asp Ala Leu Asp Arg
                35                  40                  45
Phe Leu Cys Thr His Ile Ile Tyr Ser Phe Ala Asn Ile Ser Asn Asp
            50                  55                  60
His Ile Asp Thr Trp Glu Trp Asn Asp Val Thr Leu Tyr Gly Met Leu
65                  70                  75                  80
Asn Thr Leu Lys Asn Arg Asn Pro Asn Leu Lys Thr Leu Leu Ser Val
                85                  90                  95
Gly Gly Trp Asn Phe Gly Ser Gln Arg Phe Ser Lys Ile Ala Ser Asn
                100                 105                 110
Thr Gln Ser Arg Arg Thr Phe Ile Lys Ser Val Pro Pro Phe Leu Arg
                115                 120                 125
Thr His Gly Phe Asp Gly Leu Asp Leu Ala Trp Leu Tyr Pro Gly Arg
                130                 135                 140
Arg Asp Lys Gln His Phe Thr Thr Leu Ile Lys Glu Met Lys Ala Glu
145                 150                 155                 160
Phe Ile Lys Glu Ala Gln Pro Gly Lys Lys Gln Leu Leu Leu Ser Ala
                165                 170                 175
Ala Leu Ser Ala Gly Lys Val Thr Ile Asp Ser Ser Tyr Asp Ile Ala
                180                 185                 190
Lys Ile Ser Gln His Leu Asp Phe Ile Ser Ile Met Thr Tyr Asp Phe
                195                 200                 205
His Gly Ala Trp Arg Gly Thr Thr Gly His His Ser Pro Leu Phe Arg
                210                 215                 220
Gly Gln Glu Asp Ala Ser Pro Asp Arg Phe Ser Asn Thr Asp Tyr Ala
225                 230                 235                 240
Val Gly Tyr Met Leu Arg Leu Gly Ala Pro Ala Ser Lys Leu Val Met
                245                 250                 255
Gly Ile Pro Thr Phe Gly Arg Ser Phe Thr Leu Ala Ser Ser Glu Thr
                260                 265                 270
Gly Val Gly Ala Pro Ile Ser Gly Pro Gly Ile Pro Gly Arg Phe Thr
                275                 280                 285
Lys Glu Ala Gly Thr Leu Ala Tyr Tyr Glu Ile Cys Asp Phe Leu Arg
                290                 295                 300
Gly Ala Thr Val His Arg Ile Leu Gly Gln Gln Val Pro Tyr Ala Thr
305                 310                 315                 320
Lys Gly Asn Gln Trp Val Gly Tyr Asp Asp Gln Glu Ser Val Lys Ser
                325                 330                 335
Lys Val Gln Tyr Leu Lys Asp Arg Gln Leu Ala Gly Ala Met Val Trp
                340                 345                 350
Ala Leu Asp Leu Asp Asp Phe Gln Gly Ser Phe Cys Gly Gln Asp Leu
                355                 360                 365
Arg Phe Pro Leu Thr Asn Ala Ile Lys Asp Ala Leu Ala Ala Thr
                370                 375                 380

<210> SEQ ID NO 2
<211> LENGTH: 1867
<212> TYPE: DNA
<213> ORGANISM: Homo sapiens

<400> SEQUENCE: 2
```

```
cacatagctc agttcccata aaagggctgg tttgccgcgt cggggagtgg agtgggacag    60
gtatataaag gaagtacagg gcctggggaa gaggccctgt ctaggtagct ggcaccagga   120
gccgtgggca agggaagagg ccacaccctg ccctgctctg ctgcagccag aatgggtgtg   180
aaggcgtctc aaacaggctt tgtggtcctg gtgctgctcc agtgctgctc tgcatacaaa   240
ctggtctgct actacaccag ctggtcccag taccgggaag gcgatgggag ctgcttccca   300
gatgcccttg accgcttcct ctgtacccac atcatctaca gctttgccaa tataagcaac   360
gatcacatcg acacctggga gtggaatgat gtgacgctct acggcatgct caacacactc   420
aagaacagga accccaacct gaagactctc ttgtctgtcg gaggatggaa ctttgggtct   480
caaagatttt ccaagatagc ctccaacacc cagagtcgcc ggactttcat caagtcagta   540
ccgccatttc tgcgcaccca tggctttgat gggctggacc ttgcctggct ctaccctgga   600
cggagagaca aacagcattt taccacccta atcaaggaaa tgaaggccga atttataaag   660
gaagcccagc cagggaaaaa gcagctcctg ctcagcgcag cactgtctgc ggggaaggtc   720
accattgaca gcagctatga cattgccaag atatcccaac acctggattt cattagcatc   780
atgacctacg attttcatgg agcctggcgt gggaccacag gccatcacag tcccctgttc   840
cgaggtcagg aggatgcaag tcctgacaga ttcagcaaca ctgactatgc tgtggggtac   900
atgttgaggc tgggggctcc tgccagtaag ctggtgatgg gcatcccac cttcgggagg   960 agcttcactc tggcttcttc tgagactggt gttggagccc caatctcagg accgggaatt  1020
ccaggccggt tcaccaagga ggcagggacc cttgcctact atgagatctg tgacttcctc  1080
cgcggagcca cagtccatag aatcctcggc cagcaggtcc cctatgccac caagggcaac  1140
cagtgggtag gatacgacga ccaggaaagc gtcaaaagca aggtgcagta cctgaaggac  1200
aggcagctgg cgggcgccat ggtatgggcc ctggacctgg atgacttcca gggctccttc  1260
tgcggccagg atctgcgctt ccctctcacc aatgccatca aggatgcact cgctgcaacg  1320
tagccctctg ttctgcacac agcacggggg ccaaggatgc cccgtccccc tctggctcca  1380
gctggccggg agcctgatca cctgccctgc tgagtcccag gctgagcctc agtctccctc  1440
ccttggggcc tatgcagagg tccacaacac acagatttga gctcagccct ggtgggcaga  1500
gaggtaggga tggggctgtg gggatagtga ggcatcgcaa tgtaagactc gggattagta  1560
cacacttgtt gattaatgga aatgtttaca gatccccaag cctggcaagg gaatttcttc  1620
aactccctgc cccccagccc tccttatcaa aggacaccat tttggcaagc tctatcacca  1680
aggagccaaa catcctacaa gacacagtga ccatactaat tataccccct gcaaagccca  1740
gcttgaaacc ttcacttagg aacgtaatcg tgtccctat cctacttccc cttcctaatt  1800
ccacagctgc tcaataaagt acaagagctt aacagtgaaa aaaaaaaaaa aaaaaaaaa  1860 aaaaaaa                                                             1867
```

<210> SEQ ID NO 3
<211> LENGTH: 5
<212> TYPE: PRT
<213> ORGANISM: Mus musculus

<400> SEQUENCE: 3

Ser Tyr Asn Met His
1               5

<210> SEQ ID NO 4
<211> LENGTH: 17
<212> TYPE: PRT

-continued

<213> ORGANISM: Mus musculus

<400> SEQUENCE: 4

Leu Ile Ser Pro Gly Asn Gly Asp Thr Ser Tyr Asn Gln Lys Phe Lys
1               5                   10                  15

Gly

<210> SEQ ID NO 5
<211> LENGTH: 14
<212> TYPE: PRT
<213> ORGANISM: Mus musculus

<400> SEQUENCE: 5

Gly Gly Pro Thr Val Val Ala His Tyr Tyr Ala Met Asp Tyr
1               5                   10

<210> SEQ ID NO 6
<211> LENGTH: 10
<212> TYPE: PRT
<213> ORGANISM: Mus musculus

<400> SEQUENCE: 6

Ser Ala Ser Ser Arg Val Ser Tyr Met His
1               5                   10

<210> SEQ ID NO 7
<211> LENGTH: 7
<212> TYPE: PRT
<213> ORGANISM: Mus musculus

<400> SEQUENCE: 7

Asp Thr Ser Asn Leu Ala Ser
1               5

<210> SEQ ID NO 8
<211> LENGTH: 9
<212> TYPE: PRT
<213> ORGANISM: Mus musculus

<400> SEQUENCE: 8

Gln Gln Trp Ser Ser Asn Pro Leu Thr
1               5

<210> SEQ ID NO 9
<211> LENGTH: 123
<212> TYPE: PRT
<213> ORGANISM: Mus musculus

<400> SEQUENCE: 9

Gln Val Gln Leu Gln Gln Thr Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Leu Lys Gln Thr Pro Gly Gln Gly Leu Glu Trp Ile
        35                  40                  45

Gly Leu Ile Ser Pro Gly Asn Gly Asp Thr Ser Tyr Asn Gln Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

```
Ala Arg Gly Gly Pro Thr Val Val Ala His Tyr Tyr Ala Met Asp Tyr
            100                 105                 110

Trp Gly Gln Gly Thr Ser Val Thr Val Ser Ser
        115                 120

<210> SEQ ID NO 10
<211> LENGTH: 106
<212> TYPE: PRT
<213> ORGANISM: Mus musculus

<400> SEQUENCE: 10

Gln Ile Val Leu Thr Gln Ser Pro Ala Ile Met Ser Ala Ser Pro Gly
1               5                   10                  15

Glu Arg Val Thr Met Thr Cys Ser Ala Ser Ser Arg Val Ser Tyr Met
            20                  25                  30

His Trp Tyr Gln Gln Lys Ser Gly Thr Ser Pro Lys Arg Trp Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 11
<211> LENGTH: 447
<212> TYPE: PRT
<213> ORGANISM: Mus musculus

<400> SEQUENCE: 11

Gln Val Gln Leu Gln Gln Thr Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Leu Lys Gln Thr Pro Gly Gln Gly Leu Glu Trp Ile
        35                  40                  45

Gly Leu Ile Ser Pro Gly Asn Gly Asp Thr Ser Tyr Asn Gln Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Pro Thr Val Val Ala His Tyr Tyr Ala Met Asp Tyr
            100                 105                 110

Trp Gly Gln Gly Thr Ser Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190
```

Val Pro Ser Ser Thr Trp Pro Ser Glu Thr Val Thr Cys Asn Val Ala
            195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Val Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445

<210> SEQ ID NO 12
<211> LENGTH: 213
<212> TYPE: PRT
<213> ORGANISM: Mus musculus

<400> SEQUENCE: 12

Gln Ile Val Leu Thr Gln Ser Pro Ala Ile Met Ser Ala Ser Pro Gly
1               5                   10                  15

Glu Arg Val Thr Met Thr Cys Ser Ala Ser Ser Arg Val Ser Tyr Met
            20                  25                  30

His Trp Tyr Gln Gln Lys Ser Gly Thr Ser Pro Lys Arg Trp Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

```
Ala Ser Val Val Cys Phe Leu Asn Asn Phe Tyr Pro Lys Asp Ile Asn
        130                 135                 140
Val Lys Trp Lys Ile Asp Gly Ser Glu Arg Gln Asn Gly Val Leu Asn
145                 150                 155                 160
Ser Trp Thr Asp Gln Asp Ser Lys Asp Ser Thr Tyr Ser Met Ser Ser
                165                 170                 175
Thr Leu Thr Leu Thr Lys Asp Glu Tyr Glu Arg His Asn Ser Tyr Thr
            180                 185                 190
Cys Glu Ala Thr His Lys Thr Ser Thr Ser Pro Ile Val Lys Ser Phe
        195                 200                 205
Asn Arg Asn Glu Cys
    210

<210> SEQ ID NO 13
<211> LENGTH: 5
<212> TYPE: PRT
<213> ORGANISM: Mus musculus

<400> SEQUENCE: 13

Asp Tyr Ser Met His
1               5

<210> SEQ ID NO 14
<211> LENGTH: 17
<212> TYPE: PRT
<213> ORGANISM: Mus musculus

<400> SEQUENCE: 14

Trp Ile Asn Thr Glu Thr Gly Glu Pro Thr Tyr Ala Asp Asp Phe Lys
1               5                   10                  15
Gly

<210> SEQ ID NO 15
<211> LENGTH: 10
<212> TYPE: PRT
<213> ORGANISM: Mus musculus

<400> SEQUENCE: 15

Glu Tyr Gly Asn Tyr Glu Gly Phe Val Tyr
1               5                   10

<210> SEQ ID NO 16
<211> LENGTH: 15
<212> TYPE: PRT
<213> ORGANISM: Mus musculus

<400> SEQUENCE: 16

Arg Ala Ser Lys Ser Val Ser Thr Ser Gly Tyr Ser Tyr Met His
1               5                   10                  15

<210> SEQ ID NO 17
<211> LENGTH: 7
<212> TYPE: PRT
<213> ORGANISM: Mus musculus

<400> SEQUENCE: 17

Leu Ala Ser Asn Leu Glu Ser
1               5

<210> SEQ ID NO 18
<211> LENGTH: 9
```

<212> TYPE: PRT
<213> ORGANISM: Mus musculus

<400> SEQUENCE: 18

Gln His Ser Arg Glu Leu Pro Trp Thr
1               5

<210> SEQ ID NO 19
<211> LENGTH: 119
<212> TYPE: PRT
<213> ORGANISM: Mus musculus

<400> SEQUENCE: 19

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Met His Trp Val Lys Gln Thr Pro Gly Lys Gly Leu Lys Trp Met
            35                  40                  45

Val Trp Ile Asn Thr Glu Thr Gly Glu Pro Thr Tyr Ala Asp Asp Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Glu Tyr Gly Asn Tyr Glu Gly Phe Val Tyr Trp Gly Gln Gly
            100                 105                 110

Thr Leu Val Thr Val Ser Ala
        115

<210> SEQ ID NO 20
<211> LENGTH: 111
<212> TYPE: PRT
<213> ORGANISM: Mus musculus

<400> SEQUENCE: 20

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
                20                  25                  30

Gly Tyr Ser Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Trp Thr Phe Gly Gly Gly Thr Lys Leu Glu Ile Lys
            100                 105                 110

<210> SEQ ID NO 21
<211> LENGTH: 443
<212> TYPE: PRT
<213> ORGANISM: Mus musculus

<400> SEQUENCE: 21

Gln Ile Gln Leu Val Gln Ser Gly Pro Glu Leu Lys Lys Pro Gly Glu
1               5                   10                  15

```
Thr Val Lys Ile Ser Cys Lys Ala Ser Gly Tyr Thr Asp Tyr
             20              25              30

Ser Met His Trp Val Lys Gln Thr Pro Gly Lys Gly Leu Lys Trp Met
         35              40              45

Val Trp Ile Asn Thr Glu Thr Gly Glu Pro Thr Tyr Ala Asp Asp Phe
     50              55              60

Lys Gly Arg Phe Ala Phe Ser Leu Glu Thr Ser Ala Ser Thr Ala Tyr
 65              70              75              80

Leu Gln Ile Asn Asn Leu Lys Asn Glu Asp Thr Ala Thr Tyr Phe Cys
                 85              90              95

Ala Arg Glu Tyr Gly Asn Tyr Glu Gly Phe Val Tyr Trp Gly Gln Gly
             100             105             110

Thr Leu Val Thr Val Ser Ala Ala Lys Thr Thr Pro Pro Ser Val Tyr
         115             120             125

Pro Leu Ala Pro Gly Ser Ala Ala Gln Thr Asn Ser Met Val Thr Leu
     130             135             140

Gly Cys Leu Val Lys Gly Tyr Phe Pro Glu Pro Val Thr Val Thr Trp
145             150             155             160

Asn Ser Gly Ser Leu Ser Ser Gly Val His Thr Phe Pro Ala Val Leu
                 165             170             175

Gln Ser Asp Leu Tyr Thr Leu Ser Ser Ser Val Thr Val Pro Ser Ser
             180             185             190

Thr Trp Pro Ser Glu Thr Val Thr Cys Asn Val Ala His Pro Ala Ser
         195             200             205

Ser Thr Lys Val Asp Lys Lys Ile Val Pro Arg Asp Cys Gly Cys Lys
     210             215             220

Pro Cys Ile Cys Thr Val Pro Glu Val Ser Ser Val Phe Ile Phe Pro
225             230             235             240

Pro Lys Pro Lys Asp Val Leu Thr Ile Thr Leu Thr Pro Lys Val Thr
                 245             250             255

Cys Val Val Val Asp Ile Ser Lys Asp Asp Pro Glu Val Gln Phe Ser
             260             265             270

Trp Phe Val Asp Asp Val Glu Val His Thr Ala Gln Thr Gln Pro Arg
         275             280             285

Glu Glu Gln Phe Asn Ser Thr Phe Arg Ser Val Ser Glu Leu Pro Ile
     290             295             300

Met His Gln Asp Trp Leu Asn Gly Lys Glu Phe Lys Cys Arg Val Asn
305             310             315             320

Ser Ala Ala Phe Pro Ala Pro Ile Glu Lys Thr Ile Ser Lys Thr Lys
                 325             330             335

Gly Arg Pro Lys Ala Pro Gln Val Tyr Thr Ile Pro Pro Lys Glu
             340             345             350

Gln Met Ala Lys Asp Lys Val Ser Leu Thr Cys Met Ile Thr Asp Phe
         355             360             365

Phe Pro Glu Asp Ile Thr Val Glu Trp Gln Trp Asn Gly Gln Pro Ala
     370             375             380

Glu Asn Tyr Lys Asn Thr Gln Pro Ile Met Asp Thr Asp Gly Ser Tyr
385             390             395             400

Phe Val Tyr Ser Lys Leu Asn Val Gln Lys Ser Asn Trp Glu Ala Gly
                 405             410             415

Asn Thr Phe Thr Cys Ser Val Leu His Glu Gly Leu His Asn His
             420             425             430
```

Thr Glu Lys Ser Leu Ser His Ser Pro Gly Lys
            435                 440

<210> SEQ ID NO 22
<211> LENGTH: 218
<212> TYPE: PRT
<213> ORGANISM: Mus musculus

<400> SEQUENCE: 22

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Trp Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 23
<211> LENGTH: 369
<212> TYPE: DNA
<213> ORGANISM: Mus musculus

<400> SEQUENCE: 23
caggtgcaac tgcagcagac tggggctgag ctggtgaagc ctggggcctc agtgaagatg      60
tcctgcaagg cttctggcta cacatttacc agttacaata tgcactggct aaagcagaca     120
cctggacagg gcctggaatg gattggactt atttctccag gaaatggtga tacttcctac     180
aatcagaagt tcaaaggcaa ggccacattg actgcagaca atcctccaa cacagcctac      240 atgcagctca gtagcctgac atctgaggac tctgcggtct atttctgtgc aagagggggg     300
cctacggtag tagcccatta ctatgctatg gactactggg gtcagggaac ctcagtcacc     360
gtctcctca                                                             369

<210> SEQ ID NO 24
<211> LENGTH: 318
<212> TYPE: DNA

<213> ORGANISM: Mus musculus

<400> SEQUENCE: 24

| | | | | | | |
|---|---|---|---|---|---|---|
| caaattgttc | tcacccagtc | tccagcaatc | atgtctgcat | ctccagggga | gagggtcacc | 60 |
| atgacctgca | gtgccagctc | acgtgtaagt | tacatgcact | ggtaccagca | gaagtcaggc | 120 |
| acctccccca | aaagatggat | ttatgacaca | tccaacctgg | cttctggagt | ccctgctcgc | 180 |
| ttcagtggca | gtgggtctgg | gacctcttac | tctctcacaa | tcagcaccat | ggaggctgaa | 240 |
| gatgctgcca | cttattactg | ccagcagtgg | agtagtaacc | cgctcacgtt | cggtgctggg | 300 |
| accaagctgg | agctgaaa | | | | | 318 |

<210> SEQ ID NO 25
<211> LENGTH: 1341
<212> TYPE: DNA
<213> ORGANISM: Mus musculus

<400> SEQUENCE: 25

| | | | | | | |
|---|---|---|---|---|---|---|
| caggtgcaac | tgcagcagac | tggggctgag | ctggtgaagc | ctggggcctc | agtgaagatg | 60 |
| tcctgcaagg | cttctggcta | cacatttacc | agttacaata | tgcactggct | aaagcagaca | 120 |
| cctggacagg | gcctggaatg | gattggactt | atttctccag | gaaatggtga | tacttcctac | 180 |
| aatcagaagt | tcaaaggcaa | ggccacattg | actgcagaca | aatcctccaa | cacagcctac | 240 |
| atgcagctca | gtagcctgac | atctgaggac | tctgcggtct | atttctgtgc | aagaggggggg | 300 |
| cctacggtag | tagcccatta | ctatgctatg | gactactggg | gtcagggaac | ctcagtcacc | 360 |
| gtctcctcag | ccaaaacgac | accccccatct | gtctatccac | tggcccctgg | atctgctgcc | 420 |
| caaactaact | ccatggtgac | cctgggatgc | ctggtcaagg | gctatttccc | tgagccagtg | 480 |
| acagtgacct | ggaactctgg | atccctgtcc | agcggtgtgc | acaccttccc | agctgtcctg | 540 |
| cagtctgacc | tctacactct | gagcagctca | gtgactgtcc | cctccagcac | ctggcccagc | 600 |
| gagaccgtca | cctgcaacgt | tgcccacccg | gccagcagca | ccaaggtgga | caagaaaatt | 660 |
| gtgcccaggg | attgtggttg | taagccttgc | atatgtacag | tcccagaagt | atcatctgtc | 720 |
| ttcatcttcc | ccccaaagcc | caaggatgtg | ctcaccatta | ctctgactcc | taaggtcacg | 780 |
| tgtgttgtgg | tagacatcag | caaggatgat | cccgaggtcc | agttcagctg | gtttgtagat | 840 |
| gatgtggagg | tgcacacagc | tcagacgcaa | ccccgggagg | agcagttcaa | cagcactttc | 900 |
| cgctcagtca | gtgaacttcc | catcatgcac | caggactggc | tcaatggcaa | ggagttcaaa | 960 |
| tgcagggtca | acagtgcagc | tttccctgcc | cccatcgaga | aaaccatctc | caaaaccaaa | 1020 |
| ggcagaccga | aggctccaca | ggtgtacacc | attccacctc | caaggagcaa | gatggccaag | 1080 |
| gataaagtca | gtctgacctg | catgataaca | gacttcttcc | ctgaagacat | tactgtggag | 1140 |
| tggcagtgga | atgggcagcc | agcggagaac | tacaagaaca | ctcagcccat | catggacaca | 1200 |
| gatggctctt | acttcgtcta | cagcaagctc | aatgtgcaga | gagcaactg | ggaggcagga | 1260 |
| aatactttca | cctgctctgt | gttacatgag | ggcctgcaca | accaccatac | tgagaagagc | 1320 |
| ctctcccact | ctcctggtaa | a | | | | 1341 |

<210> SEQ ID NO 26
<211> LENGTH: 639
<212> TYPE: DNA
<213> ORGANISM: Mus musculus

<400> SEQUENCE: 26

| | | | | | | |
|---|---|---|---|---|---|---|
| caaattgttc | tcacccagtc | tccagcaatc | atgtctgcat | ctccagggga | gagggtcacc | 60 |

```
atgacctgca gtgccagctc acgtgtaagt tacatgcact ggtaccagca gaagtcaggc    120
acctccccca aaagatggat ttatgacaca tccaacctgg cttctggagt ccctgctcgc    180
ttcagtggca gtgggtctgg gacctcttac tctctcacaa tcagcaccat ggaggctgaa    240
gatgctgcca cttattactg ccagcagtgg agtagtaacc cgctcacgtt cggtgctggg    300
accaagctgg agctgaaacg ggctgatgct gcaccaactg tatccatctt cccaccatcc    360
agtgagcagt taacatctgg aggtgcctca gtcgtgtgct tcttgaacaa cttctacccc    420
aaagacatca atgtcaagtg gaagattgat ggcagtgaac gacaaaatgg cgtcctgaac    480
agttggactg atcaggacag caaagacagc acctacagca tgagcagcac cctcacgttg    540
accaaggacg agtatgaacg acataacagc tatacctgtg aggccactca caagacatca    600
acttcaccca ttgtcaagag cttcaacagg aatgagtgt                          639

<210> SEQ ID NO 27
<211> LENGTH: 357
<212> TYPE: DNA
<213> ORGANISM: Mus musculus

<400> SEQUENCE: 27
cagatccagt tggtgcagtc tggacctgag ctgaagaagc ctggagagac agtcaagatc     60
tcctgcaagg cttctggtta taccttcaca gactattcaa tgcactgggt gaaacagact    120
ccaggaaagg gtttaaagtg gatggtctgg ataaacactg agactggtga gccaacatat    180
gcagatgact tcaagggacg gtttgccttc tcctttggaaa cctctgccag caccgcctat    240
ttgcagatca acaacctcaa aaatgaggac acggctacat atttctgtgc tagagagtat    300
ggaaactacg aggggtttgt ttactggggc caagggactc tggtcactgt ctctgca       357

<210> SEQ ID NO 28
<211> LENGTH: 333
<212> TYPE: DNA
<213> ORGANISM: Mus musculus

<400> SEQUENCE: 28
gacattgtgc tgacacagtc tcctgcttcc ttagctgtat ctctggggca gagggccacc     60
atctcatgca gggccagcaa aagtgtcagt acatctggct atagttatat gcactggtac    120
caacagaaac caggacagcc acccaaactc ctcatctatc ttgcatccaa cctagaatct    180
ggggtccctg ccaggttcag tggcagtggg tctgggacag acttcaccct caacatccat    240
cctgtggagg aggaggatgc tgcaacctat tactgtcagc acagtaggga gcttccgtgg    300
acgttcggtg gaggcaccaa gctggaaatc aaa                                333

<210> SEQ ID NO 29
<211> LENGTH: 1329
<212> TYPE: DNA
<213> ORGANISM: Mus musculus

<400> SEQUENCE: 29
cagatccagt tggtgcagtc tggacctgag ctgaagaagc ctggagagac agtcaagatc     60
tcctgcaagg cttctggtta taccttcaca gactattcaa tgcactgggt gaaacagact    120
ccaggaaagg gtttaaagtg gatggtctgg ataaacactg agactggtga gccaacatat    180
gcagatgact tcaagggacg gtttgccttc tcctttggaaa cctctgccag caccgcctat    240
ttgcagatca acaacctcaa aaatgaggac acggctacat atttctgtgc tagagagtat    300
```

```
ggaaactacg agggggtttgt ttactggggc caagggactc tggtcactgt ctctgcagcc    360
aaaacgacac ccccatctgt ctatccactg gcccctggat ctgctgccca aactaactcc    420
atggtgaccc tgggatgcct ggtcaagggc tatttccctg agccagtgac agtgacctgg    480
aactctggat ccctgtccag cggtgtgcac accttccag ctgtcctgca gtctgacctc     540
tacactctga gcagctcagt gactgtcccc tccagcacct ggcccagcga gaccgtcacc    600
tgcaacgttg cccacccggc cagcagcacc aaggtggaca agaaaattgt gcccagggat    660
tgtggttgta agccttgcat atgtacagtc ccagaagtat catctgtctt catcttcccc    720
ccaaagccca aggatgtgct caccattact ctgactccta aggtcacgtg tgttgtggta    780
gacatcagca aggatgatcc cgaggtccag ttcagctggt ttgtagatga tgtggaggtg    840
cacacagctc agacgcaacc ccgggaggag cagttcaaca gcacttttcg ctcagtcagt    900
gaacttccca tcatgcacca ggactggctc aatggcaagg agttcaaatg cagggtcaac    960
agtgcagctt ccctgccc catcgagaaa accatctcca aaaccaaagg cagaccgaag      1020
gctccacagg tgtacaccat tccacctccc aaggagcaga tggccaagga taaagtcagt   1080
ctgacctgca tgataacaga cttcttccct gaagacatta ctgtggagtg gcagtggaat   1140
gggcagccag cggagaacta caagaacact cagcccatca tggacacaga tggctcttac   1200
ttcgtctaca gcaagctcaa tgtgcagaag agcaactggg aggcaggaaa tactttcacc   1260
tgctctgtgt tacatgaggg cctgcacaac caccatactg agaagagcct ctcccactct   1320
cctggtaaa                                                           1329

<210> SEQ ID NO 30
<211> LENGTH: 654
<212> TYPE: DNA
<213> ORGANISM: Mus musculus

<400> SEQUENCE: 30
gacattgtgc tgacacagtc tcctgcttcc ttagctgtat ctctggggca gagggccacc     60
atctcatgca gggccagcaa aagtgtcagt acatctggct atagttatat gcactggtac    120
caacagaaac caggacagcc acccaaactc ctcatctatc ttgcatccaa cctagaatct    180
ggggtccctg ccaggttcag tggcagtggg tctgggacag acttcaccct caacatccat    240
cctgtggagg aggaggatgc tgcaacctat tactgtcagc acagtaggga gcttccgtgg    300
acgttcggtg gaggcaccaa gctggaaatc aaacgggctg atgctgcacc aactgtatcc    360
atcttcccac catccagtga gcagttaaca tctggaggtg cctcagtcgt gtgcttcttg    420
aacaacttct accccaaaga catcaatgtc aagtggaaga ttgatggcag tgaacgacaa    480
aatggcgtcc tgaacagttg gactgatcag gacagcaaag acagcaccta cagcatgagc    540
agcaccctca cgttgaccaa ggacgagtat gaacgacata cagctatac ctgtgaggcc     600
actcacaaga tcaacttc acccattgtc aagagcttca acaggaatga gtgt             654
```